United States Patent
Backes et al.

(10) Patent No.: US 9,131,719 B2
(45) Date of Patent: *Sep. 15, 2015

(54) USE OF CERTAIN NEOFLAVONOIDS FOR INTENSIFYING AND/OR PRODUCING A SENSORY IMPRESSION OF SWEETNESS

(75) Inventors: Michael Backes, Holzminden (DE); Tobias Vössing, Beverungen (DE); Jakob Peter Ley, Holzminden (DE); Susanne Paetz, Höxter (DE)

(73) Assignee: SYMRISE AG, Holzminden (DE)

( * ) Notice: Subject to any disclaimer, the term of this patent is extended or adjusted under 35 U.S.C. 154(b) by 198 days.

This patent is subject to a terminal disclaimer.

(21) Appl. No.: 13/616,134

(22) Filed: Sep. 14, 2012

(65) Prior Publication Data

US 2013/0084252 A1 Apr. 4, 2013

Related U.S. Application Data

(60) Provisional application No. 61/535,127, filed on Sep. 15, 2011.

(30) Foreign Application Priority Data

Sep. 15, 2011 (EP) .................................. 11 181 511

(51) Int. Cl.

| | |
|---|---|
| A23L 1/236 | (2006.01) |
| A61K 47/22 | (2006.01) |
| A61K 8/49 | (2006.01) |
| A61Q 19/00 | (2006.01) |
| A23L 1/22 | (2006.01) |
| A23L 1/226 | (2006.01) |
| C07D 311/20 | (2006.01) |
| C07C 57/52 | (2006.01) |
| C07C 57/60 | (2006.01) |
| C07C 57/64 | (2006.01) |

(52) U.S. Cl.
CPC ........... *A23L 1/2363* (2013.01); *A23L 1/22091* (2013.01); *A23L 1/22657* (2013.01); *A23L 1/22671* (2013.01); *A61K 8/498* (2013.01); *A61K 47/22* (2013.01); *A61Q 19/00* (2013.01); *C07C 57/52* (2013.01); *C07C 57/60* (2013.01); *C07C 57/64* (2013.01); *C07D 311/20* (2013.01)

(58) Field of Classification Search
None
See application file for complete search history.

(56) References Cited

U.S. PATENT DOCUMENTS

| | | | |
|---|---|---|---|
| 7,005,146 B2 * | 2/2006 | Lee ............................... | 424/725 |
| 2008/0176912 A1 | 7/2008 | Kuo et al. | |
| 2008/0305052 A1 | 12/2008 | Ley et al. | |
| 2010/0233102 A1 | 9/2010 | Krammer et al. | |
| 2011/0160311 A1 * | 6/2011 | Prakash et al. ................ | 514/777 |

FOREIGN PATENT DOCUMENTS

| | | |
|---|---|---|
| DE | 2701280 A1 | 7/1978 |
| EP | 2 298 084 A1 | 3/2011 |

OTHER PUBLICATIONS

R.S.J. Keast and P.A.S. Breslin. An overview of binary taste-taste interactions. Food Quality and Preference 14 (2002) 111-124.*
Li Hongfang, Ma Qingyun, Liu Yuqing, Qian Jinfu, Zhou Jun & Zhao Youxing. Chemical Constituents from Polygonum perfoliatum. Chin J Appl Environ Biol. 2009, 15 ( 5 ): 615-620.*
Abu T.M. Serajuddin. Salt formation to improve drug solubility. Advanced Drug Delivery Reviews 59 (2007) 603-616.*
Property prediction cpds 7 and 8 from "Drug Relevant Properties Predictor" found online Oct. 27, 2014 from the site: http://www.rdchemicals.com/drug-relevant-properties.html.*
Roelens F. et al., "Regioselective synthesis and estrogenicity of (+/−)-8-alkyl-5,7-dihydroxy-4-(4-hydroxyphenyl)-3,4-dihydrocoumarins", European Journal of Medicinal Chemistry Editions Scientifique Elsevier, Paris, FR, vol. 40, No. 10, 2005, pp. 1042-1051, XP027857667.
European Search Report, European Application No. 11181511.4, dated Jun. 13, 2012.

* cited by examiner

*Primary Examiner* — Frederick Krass
*Assistant Examiner* — Michael P Cohen
(74) *Attorney, Agent, or Firm* — Novak Druce Connolly Bove + Quigg LLP

(57) ABSTRACT

The present invention primarily relates to the use of one or a plurality of neoflavonoids of formula (I) and/or one or a plurality of physiologically acceptable salts of one or a plurality of neoflavonoids of formula (I) for producing a sensory impression of sweetness (i.e. an impression of sweetness) in an orally consumable preparation or for intensifying the sensory impression of sweetness of an orally consumable preparation comprising at least one further sweet-tasting and/or sweet-smelling substance. The present invention further relates to certain semifinished products and certain orally consumable preparations containing one or a plurality of neoflavonoids of formula (I) and/or one or a plurality of physiologically acceptable salts of one or a plurality of neoflavonoids of formula (I). Finally the invention also relates to a method of producing an orally consumable preparation and a method of producing and/or intensifying a sensory impression of sweetness in/of an orally consumable preparation.

14 Claims, No Drawings

USE OF CERTAIN NEOFLAVONOIDS FOR INTENSIFYING AND/OR PRODUCING A SENSORY IMPRESSION OF SWEETNESS

The present invention primarily relates to the use of one or a plurality of neoflavonoids of formula (I) defined hereunder and/or one or a plurality of physiologically acceptable salts of one or a plurality of neoflavonoids of formula (I) defined hereunder for producing a sensory impression of sweetness (i.e. an impression of sweetness) in an orally consumable preparation or for intensifying the sensory impression of sweetness of an orally consumable preparation comprising at least one other sweet-tasting substance. The present invention further relates to certain semifinished products and certain orally consumable preparations containing one or a plurality of neoflavonoids of formula (I) and/or one or a plurality of physiologically acceptable salts of one or a plurality of neoflavonoids of formula (I). Finally the invention also relates to a method of producing an orally consumable preparation and a method of producing and/or intensifying a sensory impression of sweetness in/of an orally consumable preparation.

Foods and semi-luxury food products that have a high sugar content (mainly sucrose (=saccharose), lactose, glucose or fructose or mixtures thereof), are as a rule greatly preferred by consumers on account of their sweetness. However, it is generally known that a high content of carbohydrates that can be easily metabolized causes a large rise in blood sugar level, leads to the formation of fat depots and can ultimately lead to health problems such as overweight, obesity, insulin resistance, adult-onset diabetes and the sequelae thereof. In particular, a further complication is that many of the aforementioned carbohydrates can additionally have an adverse effect on dental health, as they are degraded by certain types of bacteria in the oral cavity, for example to lactic acid, and can attack the enamel of juvenile or adult teeth (caries).

Therefore it has long been an aim to reduce the sugar content of foods and/or semi-luxury food products as much as possible, and the preferred aim is to achieve this reduction with the minimum possible decrease in the impression of sweetness. A corresponding measure consists of the use of sweeteners: these are chemically homogeneous substances, which themselves have no or only a very slight calorific value and at the same time produce a strong impression of sweet taste; the substances are as a rule noncariogenic (a review is given e.g. in Journal of the American Dietetic Association 2004, 104 (2), 255-275). The so-called bulk sweeteners such as sorbitol, mannitol or other sugar alcohols are admittedly sometimes excellent sweeteners and can also partially replace the other food-processing properties of sugars, but if ingested too often, lead in a certain segment of the population to osmotically-induced digestive problems. The normutritive, highly intensive sweeteners are very suitable, owing to the low concentration at which they are used, for imparting sweetness to foodstuffs. A number of these sweeteners are not, however, of natural origin (sucralose, cyclamate, acesulfame-K, saccharin, aspartame), display taste-related problems because of different time-intensity profiles compared to sugar (e.g. sucralose, stevioside, cyclamate), a bitter and/or astringent aftertaste (e.g. acesulfame-K, saccharin, stevioside, rebaudioside), pronounced additional flavor impressions (e.g. glycerrhizinic acid ammonium salt). Some of the sweeteners are not particularly heat-resistant (e.g. thaumatin, brazzein, monellin), are not stable in all applications (e.g. aspartame) and are sometimes very long-lasting in their sweetness effect (strong sweet aftertaste, e.g. saccharin, sucralose, stevioside, rebaudioside, neotame, advantame, superaspartame).

Therefore it is desirable to find (sweet) substances that have or impart an intensive sweet taste similar to cane sugar and furthermore are stable and/or can be used widely, preferably in orally consumable preparations.

Another possibility for lowering the caloric content of foodstuffs or beverages—without the use of normutritive sweeteners—consists of reducing the sugar content of foods and/or semi-luxury food products and adding sensorily weakly perceptible or imperceptible substances, which intensify the sweetness indirectly or directly, as described e.g. in WO 2005/041684.

Such substances of natural origin (pyridinium betaines) are described in EP 1 291 342; however, they do not influence sweet taste selectively, but also other tastes such as umami or saltiness. Moreover, the substances disclosed can only be purified at high cost and/or are difficult to produce synthetically.

The use of hesperetin is recommended in WO 2007/014879 A1 and phloretin is recommended in WO 2007/107596 A1 as an intensifier of the sweet taste of reduced-sugar preparations used for nutrition or for pleasure. However, the comparatively low level of intensification of sweetness in foods and semi-luxury food products that contain high proportions of proteins, in particular denatured proteins or polysaccharides, e.g. yoghurt products, is sometimes a disadvantage when using hesperetin and phloretin. Moreover, hesperetin also has the drawback that it is not sufficiently effective in very acidic and carbonized applications such as lemonades or cola beverages.

Therefore it is also desirable to find a possible way of lowering the content of sweet compounds, in particular sweet-tasting compounds in orally consumable preparations, while the impression of sweetness remains the same, so that reduced-sugar preparations are obtained. In particular, there is a need for agents that intensify a given impression of sweetness, in particular even beyond a purely additive effect.

Accordingly, the primary aim of the present invention was to find substances (individual substances or mixtures of substances) that can produce an impression of sweetness (i.e. have intrinsic sweetness) and/or can intensify the impression of sweetness of other sweet substances.

Furthermore, corresponding orally consumable preparations should be provided, for which the impression of sweetness is produced by these substances or whose impression of sweetness is intensified by these substances while the concentration of other sweet compounds, in particular sweet-tasting compounds, is largely unaltered, or for which, while the impression of sweetness remains the same, the content of other compounds producing an impression of sweet taste is decreased, preferably with no or only slight negative sensory side-effects.

In particular, the substances imparting the required impression of sweetness or intensifying the impression of sweetness should preferably be effective even at low concentrations. Moreover, the required substances should be usable as widely as possible, i.e. it should be possible to incorporate them in many different orally usable application forms and product forms and should correspondingly be combinable and compatible with many different orally consumable base substances, auxiliaries, carriers, additives and/or active substances.

The primary aim of the present invention is achieved by using one, two or a plurality of different compounds of formula (I)

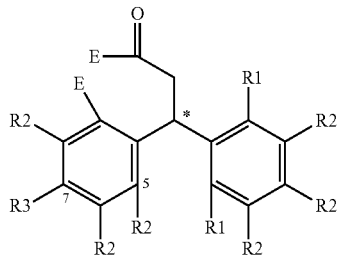

(NOTE: The figures "5" and "7" indicate positions C5 or C7 of the compound.)
or
one, two or a plurality of different physiologically acceptable salts of one, two or a plurality of different compounds of formula (I),
or
a mixture of one, two or a plurality of different compounds of formula (I) with one, two or a plurality of different physiologically acceptable salts of one, two or a plurality of different compounds of formula (I),
wherein
E either denote in each case OH or both E together denote an O,
R1, independently of the other residue R1 in each case, denotes hydrogen or $OR^a$, wherein $R^a$ is hydrogen, C1-C5 alkyl or C2-C5 alkenyl,
R2, independently of the other residues R2, denotes hydrogen or $OR^b$, wherein $R^b$ is hydrogen, C1-C5 alkyl or C2-C5 alkenyl,
wherein optionally two directly adjacent residues R1 and/or R2 together represent a group $OCH_2O$,
and
R3 denotes a residue $OR^x$, wherein $R^x$ is C1-C5 alkyl or C2-C5 alkenyl,
for producing an impression of sweetness in an orally consumable preparation or for influencing the strength of the impression of sweetness of sweet substances or mixtures of substances or of substances or mixtures of substances that are both, sweet and unpleasant, preferably bitter, tasting.

A "sweet substance or mixture of sweet substances" means, in the context of the present invention, substances and mixtures of substances producing a sensory impression of sweetness, in particular sweet-tasting substances or mixtures of substances.

The present invention preferably relates to the use of the neoflavonoids of formula (I) to be used according to the invention, mixtures thereof and/or salts thereof (in each case as defined above) for intensifying the sweet taste of a sweet-tasting substance, in particular the impression of sweetness of an orally consumable preparation comprising at least one other sweet-tasting substance.

It was found, surprisingly, that the neoflavonoids of formula (I) to be used according to the invention, mixtures thereof and/or salts thereof (in each case as defined above) can themselves produce an impression of sweetness, for example in preparations intended (i.e. suitable) for direct consumption, or significantly and markedly intensify the impression of sweetness of other sweet-tasting substances and of orally consumable preparations that contain one or a plurality of sweet-tasting substances, for example an aqueous sucrose solution.

Surprisingly, it was also found that, even at very low concentrations, the neoflavonoids of formula (I) to be used according to the invention, mixtures thereof and/or salts thereof (in each case as defined above) can greatly intensify the sweet taste or the sweet taste quality of sweet-tasting substances in orally consumable preparations according to the invention (preferably preparations to be used for nutrition, oral hygiene or pleasure or cosmetic preparations for application in the region of the head).

The neoflavonoids of formula (I) to be used according to the invention, mixtures thereof and/or salts thereof (in each case as defined above) can in particular be used for influencing the strength of taste impressions, wherein
the impression of sweet taste of a sweet-tasting substance or mixture of substances is intensified
and/or
the impression of sweet taste of a substance or mixture of substances that is both sweet and unpleasant tasting, in particular bitter tasting, is intensified and the unpleasant, in particular bitter, taste impression of the substance or mixture of substances that is both sweet and unpleasant tasting, in particular bitter tasting is reduced or masked.

In our own research it has moreover been demonstrated that the meaning of the residue R3 and its position at C7 in formula (I) is important for the effects found for the compounds to be used according to the invention, particularly for the sweetness intensifying action, in particular for the sweetness intensifying action of a sweet-tasting substance or mixture of substances. It was observed that compounds that are not to be used according to the invention, which have a residue corresponding to the residue R3 not at position C7, but with otherwise identical structure for example at position C5, display a significantly smaller sweetness intensifying action than the neoflavonoids of formula (I) to be used according to the invention (cf. practical example 1a-1 given below).

It was also found in our own research that the neoflavonoids of formula (I) to be used according to the invention, mixtures thereof and/or salts thereof (in each case as defined above) in addition can alter and mask unpleasant taste notes, and in particular have bitterness-masking properties (cf. practical example 1b given below).

"Mask or masking" means, in the context of the present text, a reduction, i.e. a decrease, or a complete suppression.

The altering or masking of the unpleasant taste impression therefore regularly means in consequence an improvement of taste, in particular with respect to bitter, astringent and/or metallic taste impressions.

The configuration on the chiral carbon atom of the compounds of formula (I) (i.e. at the position marked with "*" in the above formula (I)) can be (R) or (S). This also applies to the following account and to the structural formulas given below of the compounds to be used according to the invention.

The compounds of formula (I) can, in preferred configurations, be combined together as pure enantiomers or as mixtures of enantiomers in any desired ratio to one another. In a preferred configuration, the compounds of formula (I) are used in the form of racemic mixtures, i.e. as racemates.

Preferably R1 and R2 mean, independently of the respective other residue R1 and R2, hydrogen, hydroxyl or a residue selected from the group consisting of

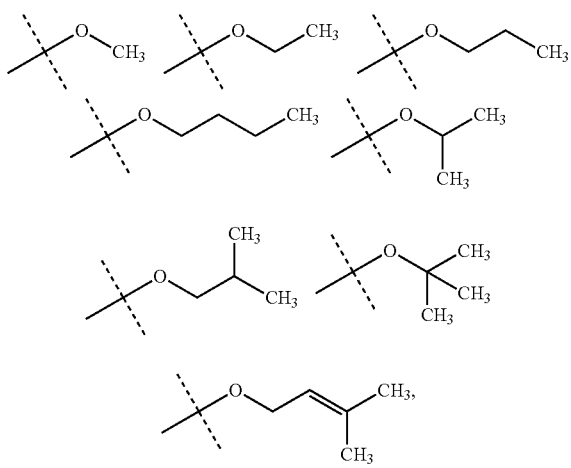

wherein the dashed line marks the bond that joins the residue to the adjacent carbon atom in formula (I).

Preferably R3 means a residue selected from the group consisting of

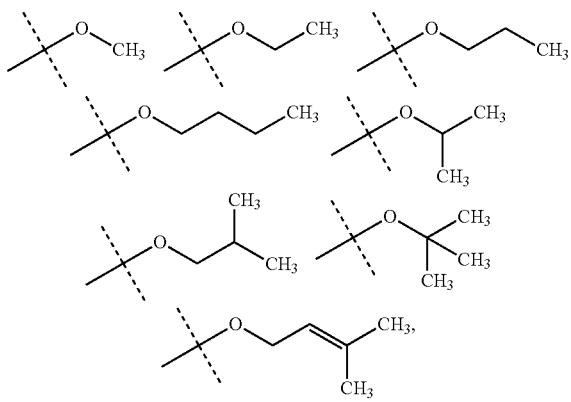

wherein the dashed line marks the bond that joins the residue to the adjacent carbon atom in formula (I).

Preferably, for the compounds of formula (I):
R1 denotes H or OH,
and
R3 is selected from the group consisting of

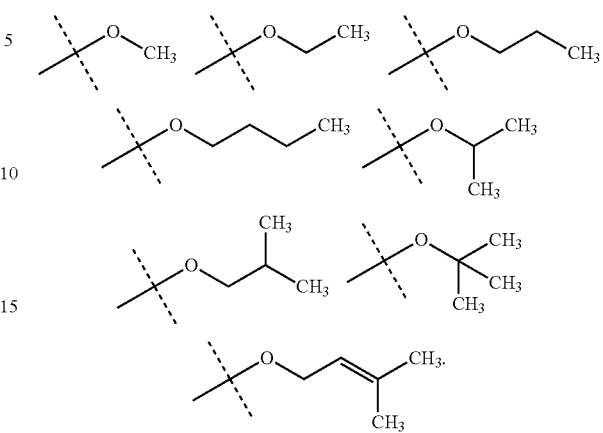

Preferred, according to the invention, is the aforementioned use, wherein one, two, a plurality of or all of the compounds used are selected in each case from the group consisting of the compounds of formula (I) and physiologically acceptable salts thereof, wherein E each denote OH or both E together denote oxygen, R1, independently of the other residue R1 in each case, denotes hydrogen or hydroxyl, R2, independently of the other residues R2, denotes hydrogen, hydroxyl, methoxy, ethoxy, n-propoxy, iso-propoxy, n-butoxy, iso-butoxy, tert-butoxy or $OR^b$, wherein $R^b$ is C5-alkenyl, and in its turn $R^b$ preferably denotes prenyl, wherein optionally two directly adjacent residues R2 together represent a group $OCH_2O$, R3 denotes methoxy, ethoxy, n-propoxy, iso-propoxy, n-butoxy, iso-butoxy, tert-butoxy or $OR^C$, wherein $R^C$ is C5-alkenyl, and in its turn $R^C$ preferably denotes prenyl, wherein preferably one or a plurality of the residues R1 or R2 denote a hydroxyl group.

The compounds to be used according to the invention of formula (I) can, depending on the meaning of E, correspond to the following structural formulas (I-A) or (I-B), wherein R1, R2 and R3 in each case have the meaning given above:

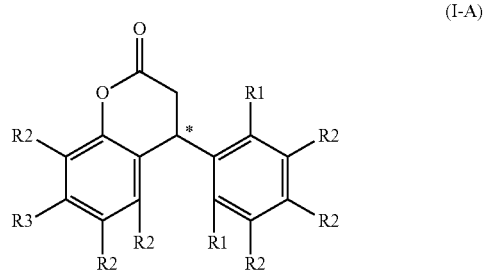

(I-A)

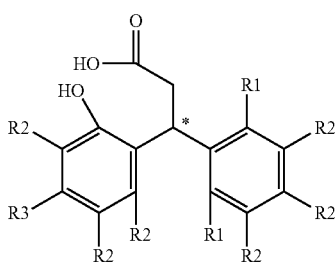
(I-B)

Depending on the pH, the lactone ring of the compound of formula (I-A) can be opened and the compound of formula (I-A) can be in equilibrium with the corresponding "open-chain" compound of formula (I-B), as shown schematically below, wherein $M^+$ denotes a (preferably physiologically acceptable) oppositely charged cation (and wherein the oppositely charged cation preferably has the meaning given below):

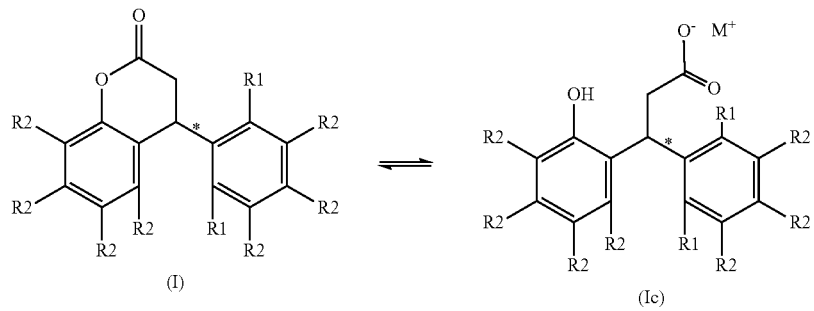

For the case when at least one of the two residues R1 in formula (I) denotes a hydroxyl group, depending on the (foodstuff) matrix and its pH—in particular in media or matrices with weakly acid pH—in most cases an equilibrium can be observed between the substances of formula (I-A1) and (I-A2).

Another aspect of the present invention relates to the use of a mixture of substances comprising one or a plurality of compounds of formula (I-A1) and one or a plurality of compounds of formula (I-A2), and/or physiologically acceptable salts thereof.

In a particularly preferred configuration, the following applies to the compounds of formula (I) and (I-A):

E each denote OH or both E together denote oxygen,
R1 denotes H,
R2, independently of the other residues R2, is selected from the group consisting of hydrogen, hydroxyl, methoxy, ethoxy, n-propoxy, iso-propoxy,
wherein optionally two directly adjacent residues R2 together represent a group $OCH_2O$,
R3 is selected from the group consisting of methoxy, ethoxy, n-propoxy and iso-propoxy,
and wherein in some preferred compounds of formula (I) or (I-A) one or a plurality of the residues R2 denote a hydroxyl group.

In some cases, the use of one or a plurality of compounds of formulas (1)-(4), physiologically acceptable salts and/or mixtures thereof, is preferred according to the invention.

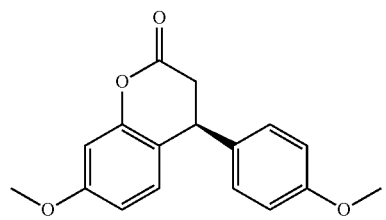
(1)

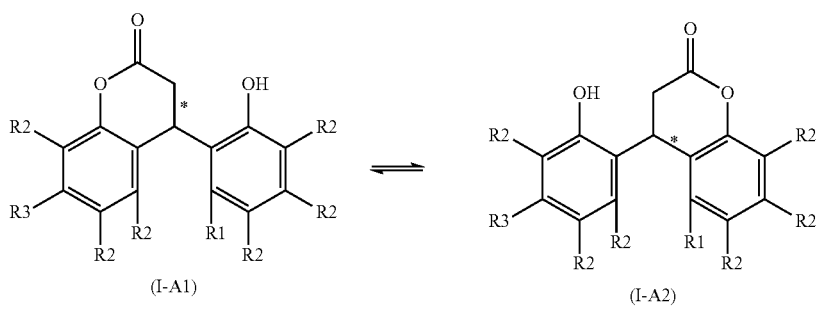

-continued (2)

(3)

(4)

(1) (4S)-7-methoxy-4-(4-methoxyphenyl)chroman-2-one
(2) (4R)-7-methoxy-4-(4-methoxyphenyl)chroman-2-one
(3) (4S)-5,7-dimethoxy-4-(4-methoxyphenyl)chroman-2-one
(4) (4R)-5,7-dimethoxy-4-(4-methoxyphenyl)chroman-2-one For the case when in an individual case there is a discrepancy between the chemical nomenclature given above and the structural formula shown in each case for the compounds of formulas (1) through (4) preferably to be used according to the invention, the structural formula applies.

In addition, generally compounds of formula (I) are preferably used according to the invention that are in each case selected from the group consisting of compounds of formula (II)

(II)

wherein
E each denote OH or both E together denote oxygen,
R2, independently of the other residues R2, denotes hydrogen, hydroxyl, methoxy, ethoxy, n-propoxy or iso-propoxy, preferably H, OH, $OCH_3$ or $OCH_2CH_3$,
wherein optionally two directly adjacent residues R2 together represent a group $OCH_2O$,
R3 denotes methoxy, ethoxy, n-propoxy, iso-propoxy, n-butoxy, iso-butoxy, tert-butoxy or $OR^C$, wherein $R^C$ is C5-alkenyl, and in its turn $R^C$ preferably denotes prenyl, and physiologically acceptable salts thereof,
wherein preferably one or a plurality of the residues R2 denote a hydroxyl group.

Also preferable is the use of compounds of formula (II-A), (II-A)

or
of a salt of a compound of formula (II-A)
or
of a mixture of two or a plurality of different compounds of formula (II-A), two or a plurality of different salts of compounds of formula (II-A) or of one or a plurality of different compounds of formula (II-A) and one or a plurality of different salts of one or a plurality of different compounds of formula (II-A),
wherein
R2, independently of the other residues R2, denotes hydrogen, hydroxyl, methoxy, ethoxy, n-propoxy or iso-propoxy, preferably H, OH, $OCH_3$ or $OCH_2CH_3$,
wherein optionally two directly adjacent residues R2 together represent a group $OCH_2O$,
R3 denotes methoxy, ethoxy, n-propoxy, iso-propoxy, n-butoxy, iso-butoxy, tert-butoxy or $OR^C$, wherein $R^C$ is C5-alkenyl, and in its turn $R^C$ preferably denotes prenyl, particularly preferably denotes methoxy, ethoxy and n-propoxy,
wherein preferably one or a plurality of residues R2 denote a hydroxyl group.

The configuration on the chiral carbon atom (i.e. at the position marked with "*" in the above formulas (II) and (II-A)) can in each case be (R) or (S).

Preferably a compound of formula (II) or a compound of formula (II-A) has a total of one, two, three or four hydroxyl groups, particularly preferably a total of one or two hydroxyl groups.

It is particularly preferable according to the invention to use one or a plurality of compounds of formulas (5)-(26) and/or physiologically acceptable salts thereof (5)

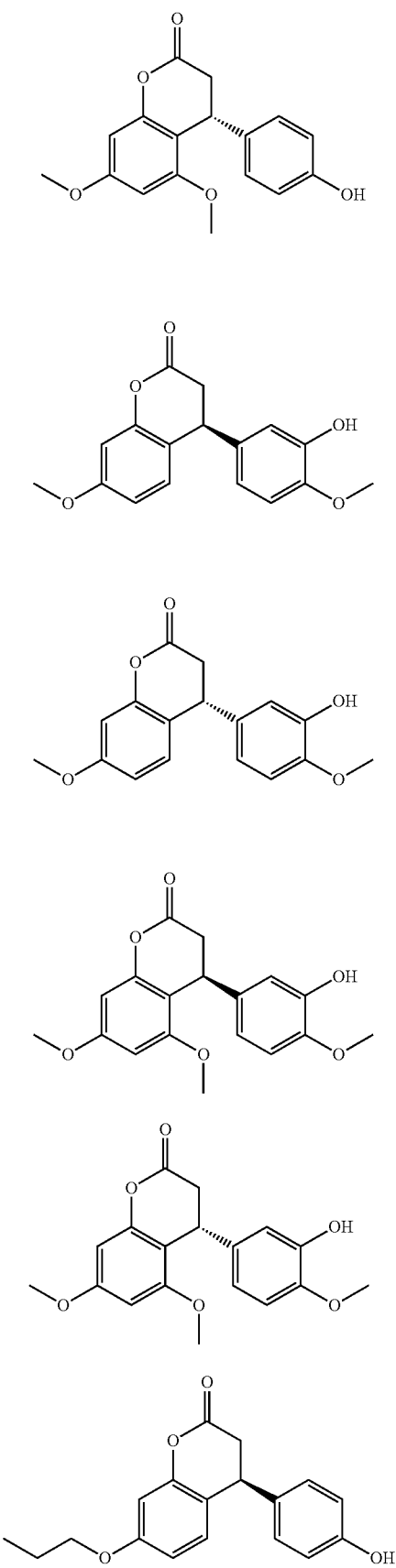
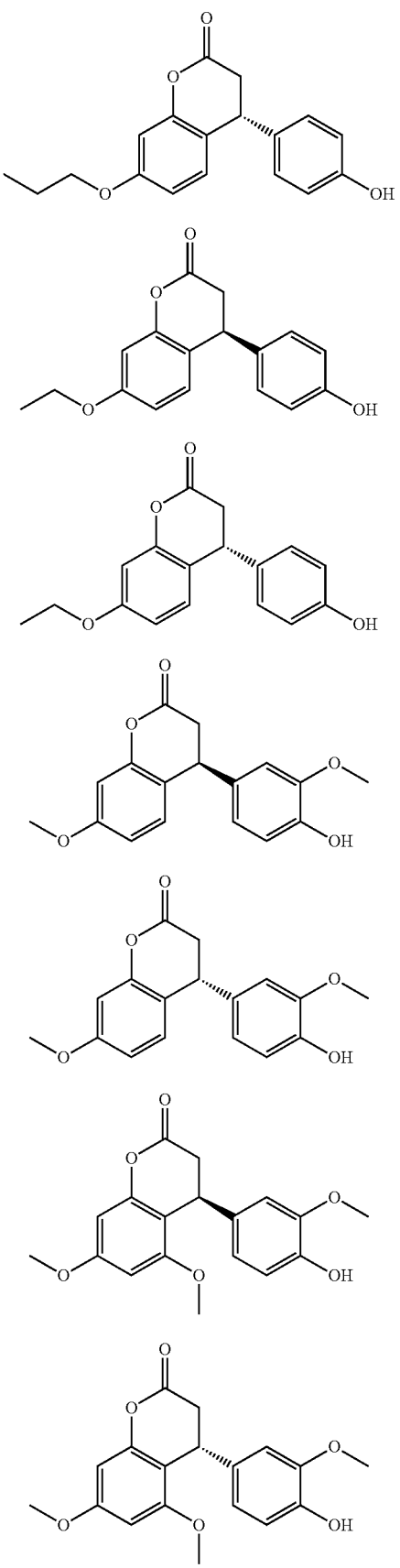

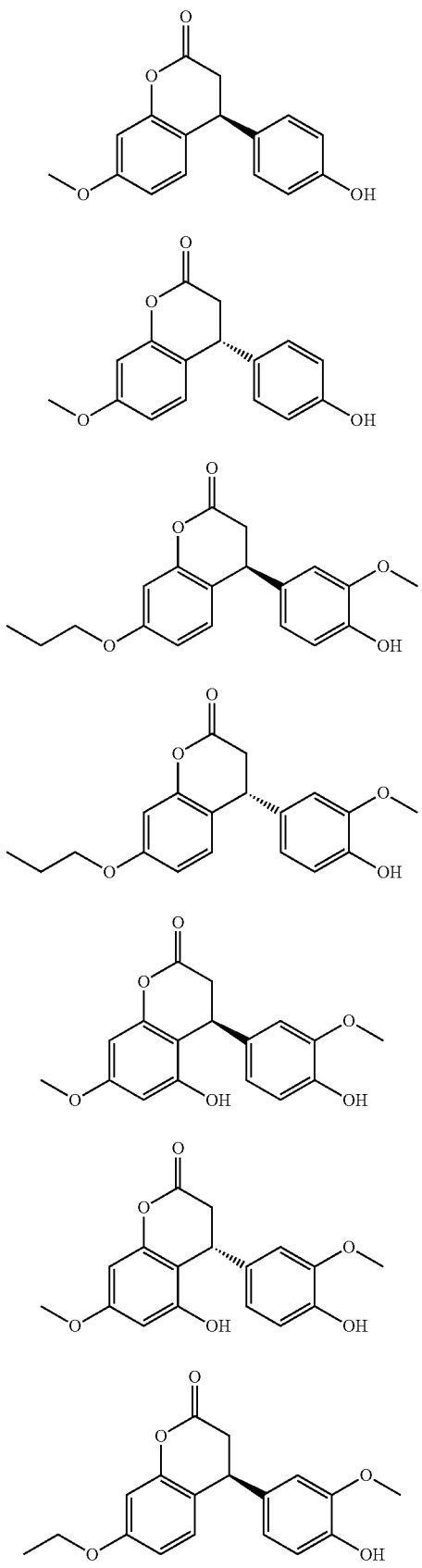
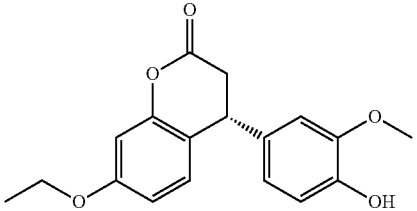

(5) (4S)-5,7-dimethoxy-4-(4-methoxyphenyl)chroman-2-one
(6) (4R)-5,7-dimethoxy-4-(4-methoxyphenyl)chroman-2-one
(7) (4S)-4-(3-hydroxy-4-methoxyphenyl)-7-methoxy-chroman-2-one
(8) (4R)-4-(3-hydroxy-4-methoxyphenyl)-7-methoxy-chroman-2-one
(9) (4S)-4-(3-hydroxy-4-methoxyphenyl)-5,7-dimethoxy-chroman-2-one
(10) (4R)-4-(3-hydroxy-4-methoxyphenyl)-5,7-dimethoxy-chroman-2-one
(11) (4S)-4-(4-hydroxyphenyl)-7-propoxy-chroman-2-one
(12) (4R)-4-(4-hydroxyphenyl)-7-propoxy-chroman-2-one
(13) (4S)-7-ethoxy-4-(4-hydroxyphenyl)chroman-2-one
(14) (4R)-7-ethoxy-4-(4-hydroxyphenyl)chroman-2-one
(15) (4S)-4-(4-hydroxy-3-methoxyphenyl)-7-methoxy-chroman-2-one
(16) (4R)-4-(4-hydroxy-3-methoxyphenyl)-7-methoxy-chroman-2-one
(17) (4S)-4-(4-hydroxy-3-methoxyphenyl)-5,7-dimethoxy-chroman-2-one
(18) (4R)-4-(4-hydroxy-3-methoxyphenyl)-5,7-dimethoxy-chroman-2-one
(19) (4S)-4-(4-hydroxyphenyl)-7-methoxy-chroman-2-one
(20) (4R)-4-(4-hydroxyphenyl)-7-methoxy-chroman-2-one
(21) (4S)-4-(4-hydroxy-3-methoxyphenyl)-7-propoxy-chroman-2-one
(22) (4R)-4-(4-hydroxy-3-methoxyphenyl)-7-propoxy-chroman-2-one
(23) (4S)-5-hydroxy-4-(4-hydroxy-3-methoxyphenyl)-7-methoxy-chroman-2-one
(24) (4R)-5-hydroxy-4-(4-hydroxy-3-methoxyphenyl)-7-methoxy-chroman-2-one
(25) (4S)-7-ethoxy-4-(4-hydroxy-3-methoxyphenyl)chroman-2-one
(26) (4R)-7-ethoxy-4-(4-hydroxy-3-methoxyphenyl)chroman-2-one Various neoflavonoids of formula (I) may also occur in certain plants or parts of plants.

The neoflavonoids (27), (28), (29) and (30) that are covered by general formula (I), and were found in *Polygonum perfoliatum* (see Planta Medica 1999, 65, 671-673; Chin. J. Appl. Environ. Biol. 2009, 15, 615-620), and physiologically acceptable salts thereof, are also preferred in the context of the present invention.

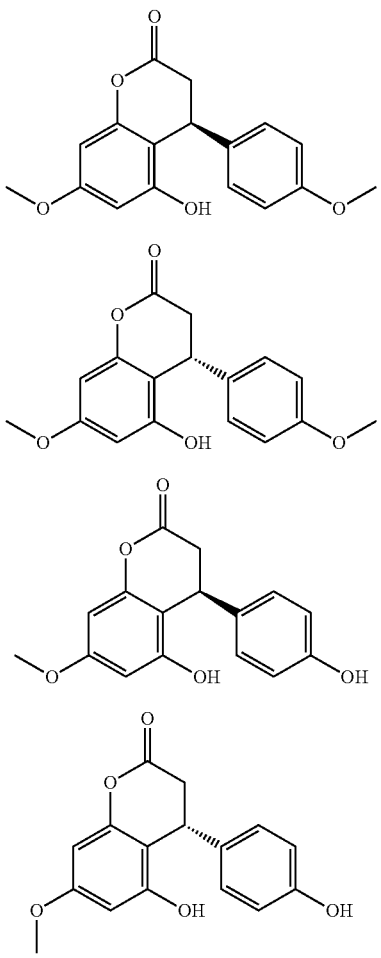

(27) (4S)-5-hydroxy-7-methoxy-4-(4-methoxyphenyl)chroman-2-one

(28) (4R)-5-hydroxy-7-methoxy-4-(4-methoxyphenyl)chroman-2-one

(29) (4S)-5-hydroxy-4-(4-hydroxyphenyl)-7-methoxy-chroman-2-one

(30) (4R)-5-hydroxy-4-(4-hydroxyphenyl)-7-methoxy-chroman-2-one

One or a plurality of the neoflavonoids of formula (I) to be used according to the invention can, if they occur naturally, also be used according to the invention in the form of plant extracts, in particular in the form of plant extracts of *Polygonum perfoliatum*.

For the case when in an individual case there is a discrepancy between the chemical nomenclature given above and the structural formula shown in each case for the compounds of formulas (5) through (30) preferably to be used according to the invention, the structural formula applies.

Compounds (1) through (30) are preferred according to the invention, compounds (5) through (30) are further preferred, and the mixtures and salts thereof defined above, wherein these can in each case be racemic mixtures, individual substances or can be combined in any desired ratio to one another.

Therefore in a preferred configuration the invention relates to the use of a compound of formulas (1)-(30), preferably a compound of formulas (5)-(30), or
of a salt of a compound of formulas (1)-(30), preferably of a compound of formulas (5)-(30),
or
of a mixture of two or a plurality of different compounds of formulas (1)-(30), preferably of a compound of formulas (5)-(30),
or
of a mixture of two or a plurality of different salts of compounds of formulas (1)-(30), preferably of a compound of formulas (5)-(30),
or
of a mixture one or a plurality of different compounds of formulas (1)-(30), preferably of a compound of formulas (5)-(30), and one or a plurality of different salts of one or a plurality of different compounds of formulas (1)-(30), preferably of a compound of formulas (5)-(30), for producing an impression of sweetness in an orally consumable preparation or for influencing the strength of the impression of sweetness of sweet substances or mixtures of substances (in particular sweet-tasting substances or mixtures of substances) or both sweet and unpleasant, preferably bitter, tasting substances or mixtures of substances, in particular for intensifying the impression of sweetness of an orally consumable preparation comprising at least one other sweet-tasting substance.

In a preferred embodiment of the present invention, R3 denotes methoxy. This applies to all aspects of the present invention, in particular to the compounds of formulas (I), (I-A), (I-A1), (I-A2), (I-B), (II) and (II-A) to be used according to the invention. Compounds of formula (II-A) that are particularly preferably to be used are therefore the compounds (5), (6), (7), (8), (9), (10), (15), (16), (17), (18), (19), (20), (23), (24), (27), (28), (29) and (30).

The compounds of formulas (I), (I-A), (I-A1), (I-A2), (I-B), (II) and (II-A) to be used according to the invention can preferably be in the form of monovalent, or (in particular in the case when a plurality of hydroxyl groups are present) polyvalent anions, wherein the cations with unipositive charge of the first main group and subgroup, the ammonium ion ($NH_4^+$), a trialkylammonium ion, the divalently charged cations of the second subgroup, and the trivalent cations of the 3rd main group and subgroup serve as oppositely charged cation. Preferably one, a plurality of or all oppositely charged cations are selected from the group consisting of $Na^+$, $K^+$, $NH_4^+$, $Ca^{2+}$, $Mf^{2+}$, $Al^{3+}$ and $Zn^{2+}$.

A chemist knows several routes for preparing the compounds of formula (I). A particularly preferred route is the acid-catalyzed reaction (classically, e.g. using sulfuric acid or hydrochloric acid) of phenol derivatives of the following formula (A) with cinnamic acid derivatives of the following formula (B) or of the corresponding esters of the following formula (C) to the compounds of formula (I) (as defined above), as outlined in the following scheme:

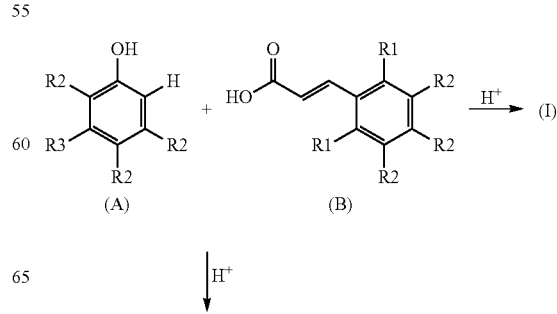

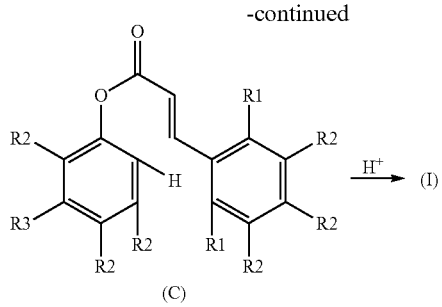

(C)

wherein in each case the residues R1, R2 and R3 have the respective meanings given above with respect to formula (I).

For example, the synthesis of compounds of formula (I) starting from 5-methoxyresorcinol is known from the literature, as described in *Synth. Commun.* 2006, 36(8) 1117-1122. Use of montmorillonite K-10 as catalyst is also conceivable, similar to the synthesis route described in *Synthesis* 2001, 15, 2247-2254.

Moreover, the neoflavanoids to be used according to the invention can also be prepared on the basis of the method described in Synth. Commun. 1987, 17(6) 723-727, as shown schematically below on the basis of the reaction of Meldrum's acid (E) with a corresponding ether of phloroglycinol (D) (wherein R3 has the meaning given above) with addition of an aldehyde (e.g. para-hydroxybenzaldehyde (F)) in the presence of pyridine to produce a racemic mixture of compounds to be used according to the invention.

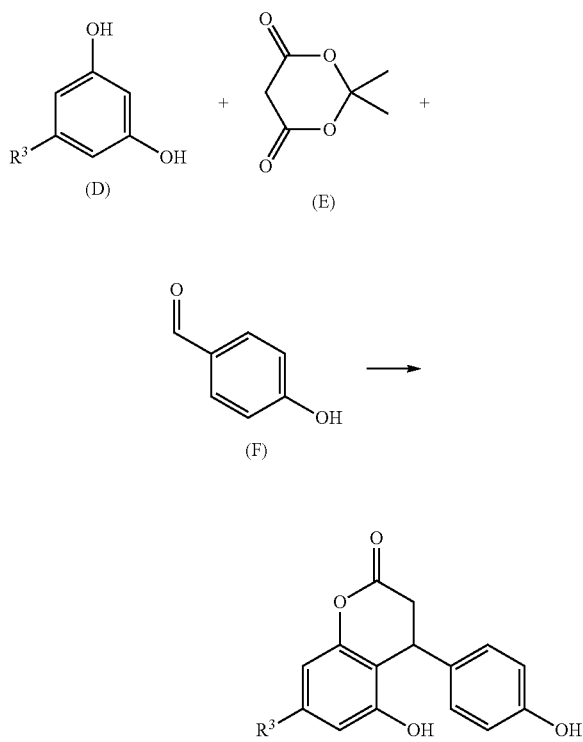

The present invention also relates to the use of the neoflavonoids of formula (I), (I-A), (I-A1), (I-A2), (I-B), (II) and (II-A) to be used according to the invention, mixtures thereof and/or salts thereof (in each case as defined above) in a preparation selected from the group consisting of (1) preparations to be used for nutrition, for food supplements, for oral hygiene or for pleasure,
(2) cosmetic preparations, in particular for application in the region of the head,
(3) pharmaceutical preparations intended to be taken orally,
(4) semifinished products, preferably flavoring compositions, for producing one of the preparations mentioned in (1) through (3).

Semifinished products in the context of the present invention are in particular in the form of flavoring compositions and/or compositions of flavoring materials or as a mixture of spices.

If the compounds to be used according to the invention occur naturally, they can also be used in the form of a plant extract.

Accordingly, the present invention also relates to the use of a product obtainable or obtained from plant material by extraction, comprising
one, two or a plurality of different compounds of formula (I) as defined above,
one, two or a plurality of different physiologically acceptable salts of one, two or a plurality of different compounds of formula (I) as defined above,
or
a mixture of one, two or a plurality of different compounds of formula (I) as defined above with one, two or a plurality of different physiologically acceptable salts of one, two or a plurality of different compounds of formula (I) as defined above,
for producing an impression of sweetness in an orally consumable preparation or for influencing the strength of the impression of sweetness of sweet substances or mixtures of substances (in particular sweet-tasting and/or sweet-smelling substances or mixtures of substances) or both sweet and unpleasant, preferably bitter, tasting substances or mixtures of substances, in particular for intensifying the impression of sweetness of an orally consumable preparation comprising at least one other sweet-tasting substance.

Said plant extract to be used according to the invention preferably contains a total proportion of 50 wt % or more, preferably of 80 wt % or more, particularly preferably of 90 wt % or more of compounds of formula (I) and salts thereof, in each case relative to the dry matter of the plant extract, wherein the compounds of formula (I) and/or salts thereof are either present as individual substances or can be combined in any proportions.

The term "dry matter" in the broader sense means the water-free and extractant-free matter of an extract to be used according to the invention. Said matter can be obtained for example by completely removing the extractant by distillation or some other evaporative technique (including the water that optionally originates from the plant material) after completion of the extraction step or steps.

The term "dry matter" in the narrower sense means the total mass of all solids of the extract, referred to 20° C. at 1013 mbar.

In the context of the present text, the "solid" state or the term "solid material" relates to 20° C. at 1013 mbar.

The invention further relates to semifinished products comprising or consisting of the following components:
(a) one or a plurality of compounds of formula (I) and/or salts thereof as defined above, preferably in one of the configurations designated as preferred or particularly preferred, and
one, two, three or a plurality of substances selected from the group consisting of the components (b) and (c)

(b) one or a plurality of sweet-tasting substances, and/or
(c) one or a plurality of substances that are both sweet and unpleasant tasting, in particular bitter tasting, and
(d) optionally one or a plurality of carriers fit for consumption,
(e) optionally one or a plurality of further substances for masking or reducing an unpleasant, in particular a bitter taste impression, and
(f) optionally one or a plurality of further substances for intensifying an impression of sweet taste,
wherein the components (b)-(f) neither are or contain a compound of formula (I) nor are or contain a salt of a compound of formula (I).

Semifinished products according to the invention, preferably flavoring compositions according to the invention, and orally consumable preparations according to the invention can, in addition to the substances of formula (I) to be used according to the invention and/or salts thereof (as defined above), contain one or a plurality of different (natural or normatural) aromatic substances and/or reactive aromas, aromatic preparations, other flavoring substances, further flavor-modulating substances, precursors, further aromatic substances, additives, sweeteners, colorants and acidifying agents, stabilizers or solvents, auxiliaries and carriers.

A semifinished product is preferred according to the invention that additionally comprises one, two, three, four, five, six, seven, eight, nine, ten or a plurality of further sweet-tasting and/or sweet-smelling substances, wherein these further sweet-tasting and/or sweet-smelling substances are preferably selected from groups (b1) through (b5) defined below.

A semifinished product that is preferred according to the invention comprises a total amount of compounds of formula (I) and physiologically acceptable salts thereof as defined above (component (a)) in the range from 0.0001 through 90 wt %, preferably in the range from 0.001 through 50 wt %, more preferably in the range from 0.01 through 40 wt %, particularly preferably in the range from 0.1 through 20 wt %, most preferably in the range from 0.2 through 10 wt %, relative to the total weight of the semifinished product.

Semifinished products according to the invention can be used for intensifying the sensory impression of sweetness, in particular the impression of sweet taste, of orally consumable finished products (i.e. of preparations intended for direct consumption), which are produced using the semifinished product according to the invention.

A preferred semifinished product according to the invention contains one or a plurality of carriers fit for consumption (component (d)) selected from the group consisting of ethanol, isopropanol, glycerol, 1,2-propylene glycol, diacetin, triacetin, edible fats, edible fatty oils, maltodextrin, gum arabic, silicon dioxide and mixtures thereof.

A further preferred semifinished product according to the invention contains one or a plurality of carriers fit for consumption selected from the group consisting of glycerol, 1,2-propylene glycol, diacetin, triacetin, edible fatty oils, maltodextrin, gum arabic, silicon dioxide and mixtures thereof.

In a preferred embodiment, a semifinished product according to the invention is characterized in that it is spray-dried.

In a preferred embodiment, a semifinished product according to the invention is characterized in that it comprises one or a plurality of solid carriers fit for consumption, i.e. constituent (d) of a semifinished product according to the invention comprises or consists of one or a plurality of solid carriers fit for consumption.

Semifinished products according to the invention in the form of flavoring compositions in the sense of the present invention contain, in addition to one or a plurality of compounds of formula (I) and/or one or a plurality of physiologically acceptable salts of these compounds, at least (i) one, two, three, four, five, six, seven, eight, nine, ten or a plurality of (further) aromatic substances (preferably selected from group (A) defined below) and/or (ii) one, two, three, four, five, six, seven or a plurality of (further) flavoring substances.

A particularly preferred semifinished product according to the invention is characterized in that the semifinished product contains two, three, four, five, six, seven, eight, nine, ten or a plurality of further aromatic substances with a molar weight above 120 g/mol, preferably with a molar weight above 125 g/mol, preferably with a molar weight in the range from 125 g/mol through 220 g/mol, in particular preferably with a molar weight in the range from 130 g/mol through 210 g/mol.

A preferred semifinished product according to the invention preferably does not contain hexane and does not contain methylene chloride, and preferably does not contain any hexane, methylene chloride, acetone or methanol.

The invention also relates to a semifinished product, preferably in the form of an aromatic composition, for producing a preparation according to the invention (as defined above), containing
  one, two or a plurality of different compounds of formula (I) as defined above, or
  one, two or a plurality of different physiologically acceptable salts of one, two or a plurality of different compounds of formula (I) as defined above, or
  a mixture of one, two or a plurality of different compounds of formula (I) as defined above with one, two or a plurality of different physiologically acceptable salts of one, two or a plurality of different compounds of formula (I) as defined above,
and
contains one, two, three, four, five, six, seven, eight, nine, ten or a plurality of further aromatic substances with a molar weight above 90 g/mol, preferably above 100 g/mol, preferably with a molar weight in the range from 110 g/mol through 300 g/mol, more preferably with a molar weight in the range from 120 g/mol through 250 g/mol, particularly preferably with a molar weight in the range from 125 g/mol through 220 g/mol, in particular preferably with a molar weight in the range from 130 g/mol through 210 g/mol,
and preferably one or a plurality of carriers fit for consumption, preferably selected from the group consisting of ethanol, isopropanol, glycerol, 1,2-propylene glycol, diacetin, triacetin, maltodextrin, gum arabic, silicon dioxide and mixtures thereof.

The configurations described above, in particular the configurations characterized above as preferred or particularly preferred, with respect to the use according to the invention of the compounds of formulas (I), (I-A), (I-A1), (I-A2), (I-B), (II) and (II-A) apply correspondingly to a semifinished product according to the invention, in particular to a preferred or particularly preferred semifinished product according to the invention.

The present invention also relates to a preparation, preferably orally consumable preparation, selected from the group consisting of
(1) preparations to be used for nutrition, for food supplements, for oral hygiene or for pleasure, (2) cosmetic preparations, in particular for application in the region of the head,
(3) pharmaceutical preparations intended to be taken orally, comprising
(i) one or a plurality of compounds of formula (I) and/or salts thereof as defined above,
and
(ii) one or a plurality of further sweet-tasting substances, one or a plurality of sweet-smelling substances and/or one or a plurality of substances that are both sweet and unpleasant tasting, in particular bitter tasting,
wherein the amount of constituent (i) in the preparation is sufficient for sensorily intensifying the impression of sweetness of the sweet-tasting and/or sweet-smelling substance or substances of constituent (ii).

A preferred preparation according to the invention, preferably an orally consumable preparation according to the invention, comprises a semifinished product as defined above, preferably in one of the configurations designated as preferred or particularly preferred.

A preferred orally consumable preparation according to the invention (as defined above) is selected from the group consisting of
(1) preparations to be used for nutrition, for food supplements, for oral hygiene or for pleasure,
(2) cosmetic preparations for application in the region of the head,
(3) pharmaceutical preparations intended to be taken orally,
wherein the orally consumable preparation (1), (2) or (3) comprises, relative to its total weight, 0.1 mg/kg (corresponding to 0.1 ppm) through 1 wt %, preferably in the range from 0.5 through 1000 mg/kg, preferably in the range from 1 through 500 mg/kg, more preferably in the range from 3 through 300 mg/kg, particularly preferably in the range from 5 through 200 mg/kg, most preferably in the range from 10 through 100 mg/kg, of compounds of formula (I) and/or salts thereof as defined above.

For determining the impression of sweetness of a compound of formula (I) to be used according to the invention, in comparison with an aqueous sucrose solution, an aqueous solution of a compound of formula (I) is prepared at the same concentration as it is present in the orally consumable preparation to be investigated. This aqueous solution is then compared and assigned with respect to taste by a group of at least five persons against a comparative series of different sucrose concentrations in water. In this way the sucrose equivalence is determined (given in sucrose (=saccharose) equivalents), i.e. the concentration of the sucrose solution whose impression of sweetness is equivalent to the impression of sweetness of the concentration of the compound of formula (I). A corresponding procedure is also followed for determining the impression of sweetness of a physiologically acceptable salt of the compound of formula (I) or of mixtures (as defined above).

Preferred concentrations of the saccharose comparative solution are 0, 0.25, 0.5, 0.75, 1, 1.5, 2, 3, 4 and 5 wt % of saccharose in water. Optionally, other concentrations, in particular higher concentrations, can also be used for the comparison series. The sucrose equivalence determined is obtained from the mean value of the individual classifications of the individual members of the panel. The members of the panel are preferably persons who have experience in the area of tasting, of varying age and sex and of varying origin.

A preferred preparation according to the invention, preferably orally consumable preparation, is characterized in that the total amount of compounds of formula (I) and/or salts thereof (as defined above) in the preparation is sufficient, in comparison with a preparation which, with otherwise identical composition, comprises neither a compound of formula (I) nor a salt of a compound of formula (I) as defined above, to impart an increase in the impression of sweetness, to be determined in sucrose equivalents, by 10% or more, preferably by 20% or more, preferably by 30% or more and particularly preferably 35% or more.

Surprisingly, it was also found that compounds of general formula (I), mixtures and/or salts thereof (as defined above) in particular in the form of the semifinished products according to the invention described above or hereunder, can reduce or even completely suppress the impression of a large number of unpleasant, in particular bitter tasting substances and orally consumable preparations that contain one or a plurality of unpleasant, in particular bitter tasting substances.

Substances causing unpleasant taste impressions in the context of this text are:
substances that taste bitter, astringent, sticky, chalky, dusty, dry, mealy, rancid and/or metallic and
substances that have a bitter, astringent, sticky, chalky, dusty, dry, mealy, rancid and/or metallic (optionally very persistent) aftertaste.

The aforementioned unpleasant tasting substances can possess further, not unpleasant taste and/or odor qualities.

Bitter substances that are to be masked according to the invention are preferably xanthines (in particular caffeine, theobromine, theophylline), phenolic glycosides (in particular salicin, arbutin), flavanoid glycosides (in particular neohesperedin, eriocitrin, neoeriocitrin, narirutin, hesperidin, naringin), chalcones or chalcone glycosides, dihydrochalcone glycosides (in particular phloridzin, trilobtain), hydrolyzable tannins (in particular gallic or ellagic acid esters of carbohydrates, e.g. pentagalloylglucose), nonhydrolyzable tannins (in particular galloylated catechins or epicatechins and oligomers thereof, e.g. proanthyocyanidins or procyanidins, thearubigenin), flavones and glycosides thereof (in particular quercetin, quercitrin, rutin, taxifolin, myricetin, myrictrin), caffeic acid or esters thereof, terpenoid bitter substances (in particular limonin, nomilin, lupolones and humolones), metallic salts (potassium chloride, sodium sulfate, magnesium salts, iron salts, aluminum salts, zinc salts), active pharmaceutical ingredients (e.g. fluoroquinolone antibiotics, paracetamol, aspirin, β-lactam antibiotics, ambroxol, propylthioracil [PROP], guaifenesin), amino acids (e.g. leucine, isoleucine, valine, tryptophan, proline, histidine, tyrosine, lysine or phenylalanine), peptides (in particular peptides with an amino acid from the group leucine, isoleucine, valine, tryptophan, proline or phenylalanine at the N- or C-terminus).

Bitter substances that are preferably masked according to the invention are selected from the group consisting of caffeine, theobromine, quinine, salicin, arbutin, neohesperedin, eriocitrin, neoeriocitrin, narirutin, hesperidin, naringin, phloridzin, catechin, epicatechin, epigallocatechin gallate (EGCG), gallocatechin, gallocatechin-3-gallate, procyanidin B2, procyanidin B5, procyanidin C1, thearubigenin, rutin, taxifolin, myricetin, myrictrin, caffeic acid or esters thereof, limonin and nomilin, amino acids (e.g. leucine, isoleucine, valine, tryptophan, proline, histidine, tyrosine, lysine or phenylalanine), peptides with an amino acid from the group leucine, isoleucine, valine, tryptophan, proline or phenylalanine on the N- or C-terminus, potassium chloride, paracetamol, aspirin and β-lactam antibiotics.

The compounds of formula (I) to be used according to the invention and the physiologically acceptable salts of the compounds of formula (I) do not have, in particular in the concentrations to be used preferably or particularly preferably according to the invention, in (preferably orally consumable) preparations according to the invention, any notable intrinsic taste, in particular in the (preferred or particularly preferred) concentrations used, they do not have any unpleasant or interfering taste notes.

In a preferred preparation according to the invention the total amount of compounds of formula (I) as defined above and of physiologically acceptable salts of the compounds of formula (I) as defined above is in the range from 0.1 mg/kg (corresponding to 0.1 ppm) through 1 wt %, preferably in the range from 0.5 through 1000 mg/kg (corresponding to 0.5 through 1000 ppm), preferably in the range from 1 through 500 mg/kg, more preferably in the range from 3 through 300 mg/kg, particularly preferably in the range from 5 through 200 mg/kg, most preferably in the range from 10 through 100 mg/kg, in each case relative to the total weight of the preparation. These ranges of amounts apply in particular to orally consumable preparations according to the invention that are intended for direct consumption.

In our own research it was also found that at much higher total concentrations used of compounds of formula (I) as defined above and of physiologically acceptable salts of the compounds of formula (I) as defined above, the sweetness intensifying effect decreases or occurs to a lesser degree. Also to that extent the aforementioned total amount of compounds of formula (I) as defined above and of physiologically acceptable salts of the compounds of formula (I) as defined above is preferred, in particular in the preferred or particularly preferred ranges of total amounts.

In particular the sweetness intensifying action of the compounds of formula (I) to be used according to the invention is observed even at a total amount of compounds of formula (I) according to the invention of less than 0.01 wt % (corresponding to 100 ppm) (ppm=parts by weight per million), preferably of less than 0.0050 wt % (corresponding to 50 ppm), in each case relative to the total weight of an orally consumable preparation according to the invention.

As already noted above, semifinished products according to the invention and orally consumable preparations according to the invention are preferred that contain one or a plurality of the aforementioned compounds of formula (I) or salts thereof that are characterized as preferred or particularly preferred.

The ethanolic-aqueous extracts of the ground whole plant *Polygonum perfoliatum* described in Planta Medica 1999, 65, 671-673 and Chin. J. Appl. Environ. Biol. 2009, 15, 615-620, as well as the fractions and mixtures of substances obtained there from the ethanolic-aqueous extracts, are not an object of the present invention.

A preferred preparation or semifinished product according to the invention is characterized in that the preparation or semifinished product is not an extract that is obtainable by extraction of the ground whole plant *Polygonum perfoliatum* with a mixture of extractants of ethanol and water in the weight or volume ratio 90:10 or 95:5, and preferably is not an extract that is obtainable by extraction of the whole plant *Polygonum perfoliatum* with a mixture of extractants of ethanol and water with a volume ratio greater than 1:1, and preferably is not an extract that is obtainable by extraction of the whole plant *Polygonum perfoliatum* with a mixture of extractants of ethanol and water.

A preferred preparation or semifinished product according to the invention preferably does not contain hexane and does not contain methylene chloride, and preferably does not contain hexane, methylene chloride, acetone or methanol.

A preferred preparation or semifinished product according to the invention is not a preparation or semifinished product that contains 4-dihydroxy-5,7-dihydroxy-4-(4-hydroxyphenyl)coumarin, α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5, bonaroside, helonioside A, helonioside B, lapathoside D, vanicoside B, vanicoside C, vanicoside F, asteryunnanoside, saikosaponin M, hydropiperoside, quercetin-3-O-β-D-glucuronide-6"-butyl ester and quercetin-3-O-β-D-glucuronide-6"-methyl ester.

Here, with respect to the structural formulas corresponding to these compounds, reference is made to the literature source Chin. J. Appl. Environ. Biol. 2009, 15, 615-620, which with respect to the corresponding compounds disclosed therein becomes part of the present application by reference.

A preferred preparation or semifinished product according to the invention is not a preparation or semifinished product that contains 4-dihydroxy-5,7-dihydroxy-4-(4-hydroxyphenyl)coumarin, α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside in the proportions by mass of 4:9:8:37:30:24:14:5:12:41.

If a preparation or semifinished product according to the invention contains 4-dihydroxy-5,7-dihydroxy-4-(4-hydroxyphenyl)coumarin, one, a plurality of or all of the following conditions apply:
 the weight ratio of 4-dihydroxy-5,7-dihydroxy-4-(4-hydroxyphenyl)coumarin to quercetin is not equal to 4:30,
 the weight ratio of 4-dihydroxy-5,7-dihydroxy-4-(4-hydroxyphenyl)coumarin to cucurbitacin IIa is not equal to 4:24,
 the weight ratio of 4-dihydroxy-5,7-dihydroxy-4-(4-hydroxyphenyl)coumarin to cucurbitacin U is not equal to 4:14,
 the weight ratio of 4-dihydroxy-5,7-dihydroxy-4-(4-hydroxyphenyl)coumarin to 7'-dihydroxymatairesinol is not equal to 4:8.

If a preparation or semifinished product according to the invention contains 4-dihydroxy-5,7-dihydroxy-4-(4-hydroxyphenyl)coumarin, the mass ratio of 4-dihydroxy-5,7-dihydroxy-4-(4-hydroxyphenyl)coumarin to the total mass of α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside is not 4:180.

A preferred preparation or semifinished product according to the invention is not a preparation or semifinished product that contains α-tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5, bonaroside, helonioside A, helonioside B, lapathoside D, vanicoside B, vanicoside C, vanicoside F, asteryunnanoside, saikosaponin M, hydropiperoside, quercetin-3-O-β-D-glucuronide-6"-butyl ester and quercetin-3-O-β-D-glucuronide-6"-methyl ester.

A preferred preparation or semifinished product according to the invention is not a preparation or semifinished product that contains α-tocopherol quinone, (24S)-ethylcholesta-3β,5α,6α-triol, cucurbitacin IIa, cucurbitacin U, iotroridoside A, pokeweedcerebroside 5 and bonaroside.

A preferred preparation or semifinished product according to the invention does not contain cucurbitacin IIa, preferably does not contain cucurbitacin IIa and does not contain cucurbitacin U, and preferably does not contain any cucurbitacins.

The configurations described above, in particular the configurations characterized above as preferred or particularly preferred, with respect to the use of the compounds of formulas (I), (I-A), (I-A1), (I-A2), (I-B), (II) and (II-A) according to the invention, apply correspondingly to a preparation or semifinished product according to the invention, in particular to a preferred or particularly preferred preparation or semifinished product according to the invention.

Method of Production
  of a semifinished product according to the invention as defined above or hereunder
or
  of a preparation according to the invention as defined above or hereunder, comprising the steps
(1) preparing or providing the following components:
  (a) one or a plurality of compounds of formula (I) and/or salts thereof as defined above,
  and
  one, two, three or a plurality of substances selected from the group consisting of the components (b) and (c)
  (b) one or a plurality of sweet-tasting substances,
  and/or
  (c) one or a plurality of substances that are both sweet and unpleasant tasting, in particular bitter tasting,
  and
  (d) optionally one or a plurality of carriers fit for consumption,
  (e) optionally one or a plurality of further substances for masking or reducing an unpleasant, in particular a bitter taste impression,
  and
  (f) optionally one or a plurality of further substances for intensifying an impression of sweet taste,
    wherein the components (b)-(f) neither are or contain a compound of formula (I) nor are or contain a salt of a compound of formula (I),
and
(2) mixing component (a) with one or a plurality of the components (b) and/or (c) and optionally (d) and optionally component (e) and optionally component (f).

In another aspect, the present invention relates to a method of influencing the strength of a sensory impression, in particular of the impression of sweetness, of a sweet-tasting and/or sweet-smelling substance or mixture of substances or a substance or mixture of substances that is both sweet and unpleasant tasting, in particular bitter tasting, with the following step:
mixing of component (a)
(a) one or a plurality of compounds of formula (I) and/or salts thereof as defined above with component (b) and/or (c)
(b) one or a plurality of sweet-tasting substances,
and/or
(c) one or a plurality of substances that are both sweet and unpleasant tasting, in particular bitter tasting,
and
(d) optionally one or a plurality of carriers fit for consumption,
(e) optionally one or a plurality of further substances for masking or reducing an unpleasant, in particular a bitter taste impression, and
(f) optionally one or a plurality of further substances for intensifying an impression of sweet taste,
  wherein the components (b)-(f) neither are or contain a compound of formula (I) nor are or contain a salt of a compound of formula (I), and
wherein the total amount of component (a) in the mixture is sufficient to influence the strength of the sensory impression, in particular of the impression of sweetness, of the sweet-tasting substance or substances of component (b) or of the both sweet and unpleasant tasting, in particular bitter tasting substance or substances of component (c).

The present invention also relates to a method for (a) imparting an impression of sweet taste and/or intensifying an impression of sweet taste of one, two or a plurality of sweet-tasting substances and/or (b) producing an orally consumable preparation according to the invention, preferably in one of the configurations characterized as preferred, with the following steps:

a) providing a compound to be used according to the invention, preferably in one of the configurations characterized as preferred, or a physiologically acceptable salt of a compound to be used according to the invention, preferably in one of the configurations characterized as preferred, a semifinished product according to the invention, preferably in one of the configurations characterized as preferred, and/or an extract to be used according to the invention, preferably in one of the configurations characterized as preferred, b) providing an orally consumable preparation, preferably comprising one, two or a plurality of further sweet-tasting substances, c) bringing in contact or mixing the constituents provided in step a) and b).

Preparations to be consumed orally according to the invention are preferred that comprise one or a plurality of compounds of formula (I) and/or one or a plurality of physiologically acceptable salts of a compound of formula (I), in a total amount that is sufficient to produce a perception of sweetness in the preparations to be consumed orally that at least corresponds to that of a comparative preparation that consists of a 2 wt % solution of sucrose in water.

Preparations to be consumed orally according to the invention are preferred that comprise one or a plurality of the compounds of formula (I) or one or a plurality of physiologically acceptable salts of a compound of formula (I) to be used according to the invention and at least one other sweet-tasting substance, wherein the latter is present at a concentration that is sufficient to produce a perception of sweetness in the preparations to be consumed orally that at least corresponds to that of a comparative preparation that consists of a 2 wt % solution of sucrose in water.

The present invention also relates to a method of intensifying the impression of sweetness of an orally consumable preparation that is formed during tasting (appraisal), comprising the steps:

a) providing an orally consumable preparation, comprising one or a plurality of further sweet-tasting substances that together impart an impression of sweetness that is equal to or stronger than that of an aqueous sucrose solution with a concentration of 2 wt % sucrose, b) providing one or a plurality of compounds of formula (I), salts or mixtures thereof (as defined above), c) mixing the constituents provided in step a) and b).

The invention also relates to a method of intensifying the sweet taste of a sweet-tasting substance with the following step:

mixing a sweet-tasting substance with an amount of one or a plurality of compounds of formula (I), salts or mixtures thereof (as defined above) that is sufficient for sensorily intensifying the impression of sweet taste of the sweet-tasting substance or substances, wherein preferably the total amount of component (a) in the mixture is sufficient to intensify, preferably synergistically intensify, the impression of sweet taste of a sweet-tasting substance or mixture of substances
and/or
to intensify the impression of sweet taste of a both sweet and unpleasant, in particular bitter tasting substance or mixture of substances synergistically and to reduce or to mask the unpleasant, in particular bitter, taste impression of the substance or mixture of substances that is both sweet and unpleasant tasting, in particular bitter tasting.

Further sweet-tasting substances in the sense of the invention can be naturally occurring sweet-tasting substances or plant extracts or else synthetic sweet-tasting substances.

Naturally occurring sweet-tasting substances (including plant extracts) can for example be sweet-tasting carbohydrates (e.g. sucrose, trehalose, lactose, maltose, melezitose, melibiose, raffinose, Palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrins), sugar alcohols (e.g. erythritol, threitol, arabitol, ribitol, xylitol, sorbitol, mannitol, maltitol, isomaltitol, dulcitol, lactitol), proteins (e.g. miraculin, pentadin, monellin, thaumatin, curculin, brazzein, mabinlin), D-amino acids (e.g. D-phenylalanine, D-tryptophan) or extracts or fractions obtained from natural sources containing these amino acids and/or proteins, neohesperidin dihydrochalcone, naringin dihydrochalcone, steviol glycoside, stevioside, steviolbioside, rebaudiosides, rebaudioside A, rebaudioside B, rebaudioside C, rebaudioside D, rebaudioside E, rebaudioside F, rebaudioside G, rebaudioside H, dulcoside, rubusoside, suavioside A, suavioside B, suavioside G, suavioside H, suavioside I, suavioside J, baiyunoside 1, baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartin, telosmoside $A_{15}$, periandrin I-V, pterocaryoside, cyclocaryoside, mukurozioside, trans-anethol, trans-cinnamaldehyde, bryoside, bryonoside, bryonodulcoside, carnosifloside, scandenosides, gypenosides, trilobtain, phloridzin, dihydroflavanole, hematoxylin, cyanin, chlorogenic acid, albiziasaponin, telosmosides, gaudichaudioside, mogrosides, mogroside V, hernandulcine, monatin, glycyrrhetin acid and derivatives thereof in particular glycyrrhizin (preferably as ammonium salt), and phyllodulcin, wherein in the case of the naturally occurring sweeteners it is also possible to use extracts or enriched fractions of these extracts, e.g. Thaumatococcus extracts (katemphe), extracts of *Stevia* ssp. (in particular *Stevia rebaudiana*), swingle extract (*Momordica* or *Siratia grosvenorii*, Luo-Han-Guo), extracts of *Glycerrhyzia* ssp. (especially *Glycerrhyzia glabra*), *Rubus* ssp. (in particular *Rubus suavissimus*), citrus extracts, extracts of *Lippia dulcis*, extracts of *Mycetia balansae* (which preferably contain balansin A and/or balansin B), as disclosed in the European patent application with the application number 11168468.4 (Symrise), which with respect to this compound becomes part of the present application by reference.

A semifinished product or an orally consumable preparation is preferred according to the invention that additionally comprises one, two, three, four, five, six, seven, eight, nine, ten or a plurality of further sweet substances, selected from the following groups (b1) through (b5):

(b1) sweet aromatic substances, wherein preferably one, two, three, four, five or a plurality of the sweet aromatic substances are selected from the group consisting of vanillin, ethylvanillin, 2-hydroxy-4-methoxybenzaldehyde, ethylvanillinisobutyrate (=3-ethoxy-4-isobutyryloxybenzaldehyde), Furaneol® (2,5-dimethyl-4-hydroxy-3(2H)-furanone) and its derivatives (preferably homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and its derivatives (preferably ethylmaltol), coumarin, gamma-lactones (preferably gamma-undecalactone, gamma-nonalactone), delta-lactones (preferably 4-methyldeltalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (preferably acetic acid-n-butyl ester, acetic acid isoamyl ester, propionic acid ethyl ester, butyric acid ethyl ester, butyric acid-n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl-3-methyl-3-phenylglycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al and phenyl acetaldehyde;

(b2) carbohydrates selected from the group consisting of sucrose, trehalose, lactose, maltose, melezitose, melibiose, raffinose, Palatinose, lactulose, O-fructose, D-glucose, D-galactose, L-rhamnose, D-sorbose, D-mannose, D-tagatose, D-arabinose, L-arabinose, D-ribose, D-glyceraldehydes, maltodextrins and plant preparations containing one or a plurality of the aforementioned carbohydrates, preferably in a proportion of at least 5 wt %, preferably at least 15 wt %, wherein the carbohydrates can also be in the form of a naturally occurring or artificially produced mixture, in particular as honey, invert-sugar syrup or highly enriched fructose syrup from corn starch, and the physiologically acceptable salts of these carbohydrates, in particular the sodium, potassium, calcium or ammonium salts;

(b3) sugar alcohols, preferably naturally occurring sugar alcohols selected from the group consisting of glycerol, erythritol, threitol, arabitol, ribitol, xylitol, sorbitol, mannitol, maltitol, isomaltitol, dulcitol, lactitol, and the physiologically acceptable salts of these sugar alcohols, in particular the sodium, potassium, calcium or ammonium salts;

(b4) naturally occurring sweeteners, preferably selected from the group consisting of (b4-1) miraculin, monellin, mabinlin, thaumatin, curculin, brazzein, pentadin, D-phenylalanine, D-tryptophan, and extracts or fractions obtained from natural sources containing these amino acids and/or proteins, and the physiologically acceptable salts of these amino acids and/or proteins, in particular the sodium, potassium, calcium or ammonium salts;

(b4-2) neohesperidin dihydrochalcone, naringin dihydrochalcone, stevioside, steviolbioside, rebaudiosides, in particular rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartin, telosmoside A15, periandrin I-V, pterocaryoside, cyclocaryoside, mukurozioside, trans-anethol, trans-cinnamaldehyde, bryoside, bryonoside, bryonodulcoside, carnosifloside, scandenosides, gypenosides, trilobtain, phloridzin, dihydroflavanols, hematoxylin, cyanin, chlorogenic acid, albiziasaponin, telosmosides, gaudichaudioside, mogrosides, mogroside V, hernandulcinen, monatin, phyllodulcin, glycyrrhetin acid and derivatives thereof, in particular glycosides thereof such as glycyrrhizin, and the physiologically acceptable salts of these compounds, in particular the sodium, potassium, calcium or ammonium salts;

(b4-3) extracts or enriched fractions of the extracts, selected from the group consisting of Thaumatococcus extracts (katemphe), extracts of *Stevia* ssp. (in particular *Stevia rebaudiana*), swingle extracts (*Momordica* or *Siratia grosvenorii*, Luo-Han-Guo), extracts of *Glycerrhyzia* ssp. (in particular *Glycerrhyzia glabra*), extracts of *Rubus* ssp. (in particular *Rubus suavissimus*), citrus extracts and extracts of *Lippia dulcis*; extracts of *Mycetia balansae;*

(b5) synthetic sweet-tasting substances, preferably selected from the group consisting of magap, sodium cyclamate or other physiologically acceptable salts of cyclamic acid, acesulfame-K or other physiologically acceptable salts, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

The aromatic substances of the above group (b1) are aromatic substances that produce a sweet odor impression. The aromatic substances of the above group (b1) do not actually taste sweet in the narrower sense, but can suggest a sweet taste in the broader sense (including odor perception).

In a preferred configuration, the total amount of compounds of formula (I) and the total amount of sweet-tasting substances of groups (b4) and (b5) defined above is in the range from 0.001 through 1 wt %, preferably in the range from 0.001 through 0.5 wt %, more preferably in the range from 0.003 through 0.1 wt %, relative to the total mass of the orally consumable preparation intended for direct consumption.

A semifinished product or an orally consumable preparation is preferred according to the invention wherein the both sweet-tasting and unpleasant-tasting substance or substances of component (c) are selected from the group consisting of steviol glycosides (in particular stevioside and rebaudioside A), rubusoside, dulcoside, mogrosides, phyllodulcin, glycyrrhetin acid, extracts of *Stevia* ssp. (in particular *Stevia rebaudiana*), Luo Han Guo, *Rubus suavissimus, Hydrangea dulcis, Glycyrrhyza glabra*, magap, sodium cyclamate, acesulfame-K, neohesperidin dihydrochalcone, naringin dihydrochalcone, saccharin, saccharin sodium salt, aspartame, superaspartame, neotame, alitame, sucralose, lugduname, carrelame, sucrononate and sucrooctate.

A preferred orally consumable preparation according to the invention comprises, in addition to a compound to be used according to the invention, in addition to a physiologically acceptable salt or in addition to a mixture to be used according to the invention (as defined above), additionally one or a plurality of further substances for intensifying an impression of sweet taste.

Further substances for intensifying the impression of sweet taste—without limiting the present invention thereto—are preferably selected from the group consisting of hydroxydeoxybenzoins, for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone (in particular as described in WO 2006/106023, which with respect to the corresponding compounds disclosed therein forms part of this application by reference); hydroxyphenylalkane dione, for example isogingerdione-[2] (in particular as described in WO 2007/003527, which with respect to the corresponding compounds disclosed therein forms part of this application by reference); diacetyl trimers (in particular as described in WO 2006/058893, which with respect to the corresponding compounds disclosed therein forms part of this application by reference); divanillins (in particular as described in WO 2004/078302, which with respect to the corresponding compounds disclosed therein forms part of this application by reference), hesperetin as disclosed in WO 2007/014879, which with respect to said compounds becomes part of the present application by reference, 4-hydroxydihydrochalcones, and in particular phloretin, as disclosed in EP 1 998 636 B1, which with respect to said compounds becomes part of the present application by reference, or propenylphenyl glycosides (chavicol glycosides) as described in EP 1 955 601 A1, which with respect to said compounds becomes part of the present application by reference, hydroxyflavans as disclosed in EP 2 253 226 A1, which with respect to said compounds becomes part of the present application by reference, certain extracts of *Hydrangea macrophylla* as disclosed in EP 2 298 084 A1, which with respect to said compounds becomes part of the present application by reference, 1-(2,4-dihydroxyphenyl)-3-(3-hydroxy-4-methoxyphenyl)-propan-1-one as disclosed in EP 2 353 403 A1, which with respect to this compound becomes part of the present application by reference and triterpenes and triterpene glycosides (balansins) and extracts of *Mycetia balansae* (preferably containing balansin A and/or balansin B) as disclosed in the European patent application with the application number 11168468.4 (Symrise), which with respect to this compound becomes part of the present application by reference.

Preferred substances intensifying sweet taste are in particular hesperetin, phloretin, 3',7-dihydroxy-4'-methoxyflavan and (S)-3',7-dihydroxy-4'-methoxyflavan, certain Hydrangea extracts or phyllodulcin, and 1-(2,4-dihydroxyphenyl)-3-(3-hydroxy-4-methoxyphenyl)-propan-1-one.

With the substances of the last-mentioned groups, further intensifying effects with respect to the impression of sweetness of the preparations according to the invention can be achieved.

A preparation according to the invention comprising one or a plurality of further aromatizing plant extracts, flavoring materials, auxiliaries or carriers is further preferred.

Of course, preferred preparations according to the invention also comprise further usual foodstuff ingredients.

In a preferred configuration, an orally consumable preparation according to the invention comprises, as sweet-tasting substance or sweet-tasting substances, one or a plurality of sweet-tasting sugars, wherein the amount of neoflavonoids of formula (I), salts thereof and/or mixtures thereof (in each case as defined above) is sufficient to impart the same or an intensified impression of sweetness, in comparison with a preparation of otherwise identical composition containing neither a compound of formula (I) nor a salt of a compound of formula (I), but comprising at least 1.05 times the amount of sugar.

An orally consumable preparation intended for direct consumption according to the invention is quite particularly preferred in which the total amount of the compounds of formula (I) is in the range from 3 ppm through 250 ppm, preferably in the range from 5 ppm through 175 ppm, particularly preferably in the range from 10 through 95 ppm, relative to the total weight of the preparation.

An orally consumable preparation according to the invention is preferred, wherein it is selected from the group consisting of pharmaceutical preparation, oral hygiene preparation, liquid and solid foodstuff preparation to be used for nutrition or for pleasure, as well as cosmetic preparations for application in the region of the head, wherein said cosmetic preparations may come in contact with the oral cavity.

Orally consumable preparations can preferably be sweet-tasting preparations to be used for nutrition, food supplements, oral hygiene or pleasure, cosmetic preparations, preferably for application in the region of the head, or oral pharmaceutical preparations (i.e. pharmaceutical preparations intended for oral administration).

A preferred semifinished product or preparation according to the invention is characterized in that the semifinished product or preparation
(i) contains one, two, three, four, five, six, seven, eight, nine, ten or a plurality of further aromatic substances with a molar weight above 90 g/mol, preferably above 100 g/mol, preferably with a molar weight in the range from 110 g/mol through 300 g/mol, more preferably with a molar weight in the range from 120 g/mol through 250 g/mol, particularly preferably with a molar weight in the range from 125 g/mol through 220 g/mol, particularly preferably with a molar weight in the range from 130 g/mol through 210 g/mol,
and/or
(ii) the semifinished product or preparation does not contain one, two, three, four, five, six, seven, eight or all of the following substances:
tocopherol quinone, 7'-dihydroxymatairesinol, (24S)-ethylcholesta-3β,5α,6α-triol, quercetin, cucurbitacin IIa, cucurbitacin U, iotroridoside A, pokeweedcerebroside 5 and bonaroside,
and/or
(iii) the semifinished product or preparation does not contain any of the following substances:
(24S)-ethylcholesta-3β,5α,6α-triol, iotroridoside A, pokeweedcerebroside 5, bonaroside, helonioside A, helonioside B, lapathoside D, vanicoside B, vanicoside C, vanicoside F, asteryunnanoside, hydropiperoside,
and/or
(iv) the semifinished product or preparation is free from fresh or dried parts of plants, in particular is free from leaves and leaf parts, of *Persicaria perfoliata* (=*Polygonum perfoliatum*).

A particularly preferred semifinished product or preparation according to the invention is characterized in that the semifinished product or preparation
(i) contains two, three, four, five, six, seven, eight, nine, ten or a plurality of further aromatic substances with a molar weight above 120 g/mol, preferably with a molar weight above 125 g/mol, preferably with a molar weight in the range from 125 g/mol through 220 g/mol, particularly preferably with a molar weight in the range from 130 g/mol through 210 g/mol.

Preferably at least two of the conditions defined above apply, preferably condition (i) and (iv) or condition (i) and (iii).

Preferably at least three of the conditions defined above apply, preferably condition (i), (ii) and (iv) or condition (i), (ii) and (iii), or all the conditions (i) through (iv).

In the context of the present invention, (further) aromatic substances to be used preferably (as constituent of a semifinished product or preparation according to the invention) are preferably selected from the following group (A) consisting of:
acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineol, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethylbutyric acid, ethyl butyrate, ethyl caprate, ethyl caproate, ethyl crotonate, ethyl furaneol, ethyl guaiacol, ethyl isobutyrate, ethyl isovalerate, ethyl lactate, ethyl methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropyl methylthiazole, lauric acid, levulinic acid, linalool, linalool oxide, linalyl acetate, menthol, menthofuran, methyl anthranilate, methyl butanol, methyl butyric acid, 2-methyl butyl acetate, methyl caproate, methyl cinnamate, 5-methylfurfural, 3,2,2-methylcyclopentenolone, 6,5,2-methylheptenone, methyldihydrojasmonate, methyl jasmonate, 2-methylmethyl butyrate, 2-methyl-2-pentenolic acid, methylthiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta-octalactone, gamma-octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegon, pulegol, sinensal, sulfurol, terpinene, terpineol, terpinols, 8,3-thiomenthanone, 4,4,2-thiomethylpentanone, thymol, delta-undecalactone, gamma-undecalactone, valencene, valeric acid, vanillin, acetoin, ethyl vanillin, ethylvanillin isobutyrate (=3-ethoxy-4-isobutyryloxybenzaldehyde), 2,5-dimethyl-4-hydroxy-3(2H)-furanone and its derivatives (here preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethylmaltol), coumarin, gamma-lactones (here preferably gamma-undecalactone, gamma-nonalactone, gamma-decalactone), delta-lactones (here preferably 4-methyldeltadecalactone, massoilactone, deltadecalactone, tuberolactone), methyl sorbate, divanillin, 4-hydroxy-2(or 5)-ethyl-5(or 2)-methyl-3(2H) furanone, 2-hydroxy-3-methyl-2-cyclopentenone, 3-hydroxy-4,5-dimethyl-2(5H)-furanone, acetic acid isoamyl ester, butyric acid ethyl ester, butyric acid-n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al, phenylacetaldehyde, 2-methyl-3-(methylthio)furan, 2-methyl-3-furanthiol, bis(2-methyl-3-furyl)disulfide, furfurylmercaptan, methional, 2-acetyl-2-thiazoline, 3-mercapto-2-pentanone, 2,5-dimethyl-3- furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamon alcohol, methyl salicylate, isopulegol and (here not explicitly named) stereoisomers, enantiomers, positional isomers, diastereomers, cis/trans isomers or epimers of these substances.

In a preferred configuration, the total amount of a semifinished product according to the invention, preferably an aromatic composition according to the invention, preferably containing one, two, three, four, five or a plurality of the aromatic substances from group (b1) defined above or from group (A), is in the range from 0.01 through 2 wt %, preferably in the range from 0.01 through 1 wt %, more preferably in the range from 0.01 through 0.5 wt %, particularly preferably in the range from 0.01 through 0.2 wt %, in each case relative to the total mass of the orally consumable preparation intended for direct consumption.

The liquid and solid foodstuff preparations in the sense of the invention used for nutrition or pleasure are for example baked products (e.g. bread, cookies, cakes, other baked goods), confectionery in the narrower sense (e.g. chocolates, chocolate bar products, other bar products, fruit gums, hard and soft toffee, chewing gum), alcoholic or nonalcoholic beverages (e.g. coffee, tea, wine, wine-containing beverages, beer, beer-containing beverages, liqueurs, spirits, brandies, fruit-containing lemonades, isotonic beverages, refreshing beverages, nectars, fruit and vegetable juices, fruit or vegetable juice preparations), instant beverages (e.g. instant-cocoa beverages, instant-tea beverages, instant-coffee beverages), meat products (e.g. ham, sausage or raw sausage preparations, spiced or marinated fresh or salted meat products), eggs or egg products (dried egg, egg white, egg yolk)), cereal products (e.g. breakfast cereals, muesli bars, precooked prepared rice products), milk products (e.g. milk drinks, milk ices, yoghurt, kefir, fresh cheese, soft cheese, hard cheese, dried milk powder, whey, butter, buttermilk, partially or fully hydrolyzed lactoprotein-containing products), products from soya protein or other soybean fractions (e.g. soya milk and products prepared therefrom, soya lecithin—containing preparations, fermented products such as tofu or tempeh or products prepared therefrom, soy sauces), fruit preparations (e.g. jellies, fruit ices, fruit sauces, fruit fillings), vegetable preparations (e.g. ketchup, sauces, dried vegetables, frozen vegetables, precooked vegetables, vegetables pickled in vinegar, preserved vegetables), nibbles (e.g. baked or fried potato chips or potato dough products, bread dough products, extruded products based on maize or peanut), fat- and oil-based products or emulsions thereof (e.g. mayonnaise, remoulade, dressings, condiment preparations), other ready-meals and soups (e.g. dried soups, instant soups, precooked soups), spices, condiment mixtures and in particular seasonings, which for example find application for snacks.

The preparations in the sense of the invention can also be in the form of capsules, tablets (uncoated and coated tablets, e.g. enteric coatings), sugar-coated pills, granules, pellets, solid mixtures, dispersions in liquid phases, as emulsions, as powders, as solutions, as pastes or as other preparations for swallowing or chewing as food supplements.

The preparations used for oral hygiene (oral hygiene products) in the sense of the present invention are in particular oral and/or dental hygiene products such as toothpastes, dental gels, dental powders, mouthwash, chewing gums and other oral hygiene products.

Oral pharmaceutical preparations in the sense of the invention are preparations that are for example in the form of capsules, tablets (uncoated and coated tablets, e.g. enteric coatings), sugar-coated pills, granules, pellets, solid mixtures, dispersions in liquid phases, as emulsions, as powders, as solutions, as pastes or as other preparations for swallowing or chewing and are used as prescription-only medicines, pharmacy-only medicines or other medicinal products or as food supplements.

Cosmetic preparations for application in the region of the head are in particular those that, when applied properly on the skin, can come in contact with the oral cavity, for example—as mentioned above—cosmetic preparations for application in the region of the head such as soaps, other cleaning or care products for the facial zone, face creams, lotions or ointments, sunscreens, beard cleaning or care products, shaving foams, soaps or gels, lipsticks or other lip cosmetics or lip care products.

Other usual active substances, base substances, auxiliaries and additives used for preparations to be used for nutrition, for oral hygiene or for pleasure, cosmetic or oral pharmaceutical preparations can be contained in amounts of up to 99.9999999 wt %, relative to the total weight of the preparation. Moreover, the preparations can contain water in an amount up to 99.99 wt %, preferably 5 through 90 wt %, relative to the total weight of the preparation.

The preparations according to the invention containing compounds of formula (I) are, according to a preferred configuration, produced by incorporating the compounds of formula (I) preferably as an aromatic composition in the form of a mixture with a solid or liquid carrier in an orally consumable base preparation. Advantageously, preparations according to the invention in the form of solution can also be transformed by spray-drying into a solid preparation.

According to another preferred embodiment, for producing orally consumable preparations according to the invention, the compounds of formula (I) or flavoring compositions containing them are also incorporated beforehand in emulsions, in liposomes, e.g. starting from phosphatidylcholine, in microspheres, in nanospheres or also in capsules, granules or extrudates from a matrix for foodstuffs and semi-luxury food products, e.g. from starch, starch derivatives, cellulose or cellulose derivatives (e.g. hydroxypropylcellulose), other polysaccharides (e.g. alginate), natural fats, natural waxes (e.g. beeswax, carnauba wax) or from proteins, e.g. gelatins.

In another preferred method of production the compounds of formula (I) or flavoring compositions containing them are complexed beforehand with one or a plurality of suitable complexing agents, for example with cyclodextrins or cyclodextrin derivatives, preferably α- or β-cyclodextrin, and are used in this complexed form.

An orally consumable preparation according to the invention, in which the matrix is selected so that the release of the compounds of formula (I) from the matrix is delayed, thus giving a long-lasting action, is particularly preferred.

As further constituents for orally consumable preparations according to the invention, it is possible to use usual base materials, auxiliaries and additives for foods and semi-luxury food products, e.g. water, mixtures of fresh or processed, plant or animal basic or raw materials (e.g. raw, baked, dried, fermented, smoked and/or boiled meat, bone, cartilage, fish, vegetables, fruit, herbs, nuts, vegetable or fruit juices or pastes or mixtures thereof), digestible or nondigestible, nonsweet carbohydrates (e.g. dextrins, amylose, amylopectin, inulin, xylans, cellulose), natural or hardened fats (e.g. tallow, lard, palm oil, coconut oil, hardened plant oil), oils (e.g. sunflower oil, peanut oil, corn oil, olive oil, fish oil, soybean oil, sesame oil), fatty acids or salts thereof (e.g. potassium stearate), proteinogenic or nonproteinogenic amino acids and related compounds (e.g. γ-aminobutyric acid, taurine), peptides (e.g. glutathione), native or processed proteins (e.g. gelatin), enzymes (e.g. peptidases), nucleic acids, nucleotides, other flavor correctants for unpleasant taste impressions, taste modulators for further, generally not unpleasant taste impressions, further flavor-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilizers (e.g. carrageenan, alginate), preservatives (e.g. benzoic acid, sorbic acid), antioxidants (e.g. tocopherol, ascorbic acid), chelating agents (e.g. citric acid), organic or inorganic acidifying agents (e.g. malic acid, acetic acid, citric acid, tartaric acid, phosphoric acid), additional bitter substances (e.g. quinine, caffeine, limonin, amarogentin, humolones, lupolones, catechins, tannins), mineral salts (e.g. sodium chloride, potassium chloride, magnesium chloride, sodium phosphates), substances preventing enzymatic browning (e.g. sulfite, ascorbic acid), essential oils, plant extracts, natural or synthetic dyes or colored pigments (e.g. carotenoids, flavonoids, anthocyans, chlorophyll and derivatives thereof), spices, trigeminally effective substances or plant extracts containing said trigeminally effective substances, synthetic, natural or nature-identical aromatic substances or odoriferous substances and odor correctants.

Dental hygiene products (as an example of preparations used for oral hygiene) generally comprise an abrasive system (abrasive or polishing medium), for example silicic acids, calcium carbonates, calcium phosphates, aluminum oxides and/or hydroxyapatites, surface-active substances e.g. sodium lauryl sulfate, sodium lauryl sarcosinate and/or cocamidopropyl betaine, humectants e.g. glycerol and/or sorbitol, thickening agents, e.g. carboxymethylcellulose, polyethylene glycols, carrageenan and/or Laponite®, flavor correctants for unpleasant taste impressions, flavor correctants for further, as a rule not unpleasant taste impressions, flavor-modulating substances (e.g. inositol phosphate, nucleotides such as guanosine monophosphate, adenosine monophosphate or other substances such as sodium glutamate or 2-phenoxypropionic acid), substances with a cooling effect e.g. menthol, menthol derivatives (e.g. L-menthol, L-menthyl lactate, L-menthyl alkyl carbonates, menthone ketals, menthane-carboxylic acid amides), 2,2,2-trialkyl acetic acid amides (e.g. 2,2-diisopropylpropionic acid methyl amide), icilin derivatives, stabilizers and active substances, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavoring materials and/or sodium bicarbonate or odor correctants.

Chewing gums (as a further example of preparations to be used for oral hygiene or pleasure) generally comprise a chewing gum base, i.e. a chewing paste that becomes plastic as it is chewed, other flavor correctants for unpleasant taste impressions, taste modulators for further, as a rule not unpleasant taste impressions, flavor-modulating substances (e.g. inositol phosphate, nucleotides such as guanosine monophosphate, adenosine monophosphate or other substances such as sodium glutamate or 2-phenoxypropionic acid), humectants, thickeners, emulsifiers, other flavoring materials and stabilizers or odor correctants.

As ingredients for oral pharmaceutical preparations according to the invention, it is possible to use all usual further active substances, base materials, excipients and additives for oral pharmaceutical preparations. As active substances it is in particular also possible to use unpleasant-tasting orally formulable active pharmaceutical ingredients. The active substances, base materials, excipients and additives can be transformed in a manner known per se into the oral dosage form. This takes place regularly using inert, non-toxic, pharmaceutically suitable excipients. These include, among others, carriers (e.g. microcrystalline cellulose), solvents (e.g. liquid polyethylene glycols), emulsifiers (e.g. sodium dodecyl sulfate), dispersing agents (e.g. polyvinylpyrrolidone), synthetic and natural biopolymers (e.g. albumin), stabilizers (e.g. antioxidants such as ascorbic acid), colorants (e.g. inorganic pigments such as iron oxides) and odor correctants and flavor correctants that do not affect the bitter taste.

Preferably, the orally consumable preparations according to the invention can also contain further aromatic substances, to round off and to improve the taste and/or odor of the preparation. Suitable flavoring compositions contain e.g. synthetic, natural or nature-identical aromas, odoriferous and/or flavoring materials and suitable auxiliaries and carriers. It is regarded as especially advantageous that any bitter or metallic taste impression present, which stems from the aromas, odoriferous and/or flavoring materials contained in the preparations according to the invention, can be reduced or suppressed and thus the overall aroma or taste profile is improved.

As already described, one aspect of the present invention relates to the use of a compound of formula (I) to be used according to the invention, a salt to be used according to the invention or a mixture to be used according to the invention (in each case as defined above), or a semifinished product according to the invention (as defined above)
  to achieve an impression of sweet taste,
  to intensify an impression of sweet taste,
and/or
  as flavor correctant.

In a particularly preferred embodiment of the invention, in addition to a compound of formula (I), a physiologically acceptable salt of a compound of formula (I), a mixture to be used according to the invention (in each case as defined above), a preparation according to the invention additionally comprises one or a plurality of further flavor correctants, i.e. one or a plurality of further substances not corresponding to formula (I) or a salt thereof, wherein the flavor correctant is suitable or the flavor correctants are suitable for
  altering or masking (where masking means reducing or completely suppressing) the unpleasant taste impression of one or a plurality of unpleasant tasting substances, or
  intensifying a pleasant taste impression, preferably another taste impression additional to an impression of sweet taste, or
  intensifying a pleasant tasting substance, preferably a pleasant tasting substance that in addition to an impression of sweet taste, imparts another pleasant taste impression.

The additional flavor correctants can preferably be selected from the following list: nucleotides (e.g. adenosine-5'-monophosphate, cytidine-5'-monophosphate) or pharmaceutically acceptable salts thereof, lactisole, sodium salts (e.g. sodium chloride, sodium lactate, sodium citrate, sodium acetate, sodium gluconoate), hydroxyflavanones, for example eriodictyol, sterubin (eriodictyol-7-methyl ether), homoeriodictyol, and sodium, potassium, calcium, magnesium or zinc salts thereof (in particular as described in EP 1 258 200 A2, which with respect to the corresponding compounds disclosed therein forms part of this application by reference), hydroxybenzoic acid amides, for example 2,4-dihydroxybenzoic acid vanillyl amide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxybenzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide-monosodium salt, 2,4-dihydroxybenzoic acid-N-2-(4-hydroxy-3-methoxyphenyl)ethyl amide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide; 4-hydroxybenzoic acid vanillyl amide (in particular as described in WO 2006/024587, which with respect to the corresponding compounds disclosed therein forms part of this application by reference); hydroxydeoxybenzoins, for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone) (in particular as described in WO 2006/106023, which with respect to the corresponding compounds disclosed therein forms part of this application by reference); hydroxyphenylalkane dione, for example gingerdione-[2], gingerdione-[3], gingerdione-[4], dehydrogingerdione-[2], dehydrogingerdione-[3], dehydrogingerdione-[4]) (in particular as described in WO 2007/003527, which with respect to the corresponding compounds disclosed therein forms part of this application by reference); diacetyl trimers (in particular as described in WO 2006/058893, which with respect to the corresponding compounds disclosed therein forms part of this application by reference); γ-aminobutyric acids (in particular as described in WO 2005/096841, which with respect to the corresponding compounds disclosed therein forms part of this application by reference); divanillins (in particular as described in WO 2004/078302, which with respect to the corresponding compounds disclosed therein forms part of this application by reference) and 4-hydroxydihydrochalcones, preferably as described in US 2008/227867 A1, which with respect to the corresponding compounds disclosed therein becomes part of the present application by reference, including in particular phloretin and davidigenin, amino acids or mixtures of whey proteins with lecithins, hesperetin as disclosed in WO 2007/014879, which with respect to said compounds becomes part of the present application by reference, 4-hydroxydihydrochalcone as disclosed in WO 2007/107596, which with respect to said compounds becomes part of the present application by reference, or propenylphenyl glycosides (chavicol glycosides) as described in EP 1 955 601 A1, which with respect to said compounds becomes part of the present application by reference, pellitorin, in particular trans-pellitorin, and flavoring compositions derived therefrom as described in EP 2 008 530 A1, which with respect to these compounds and flavoring compositions form part of this application by reference, certain extracts of Rubus suavissimus as described in U.S. provisional application 61/333,435 (Symrise) and the patent applications based thereon (e.g. the European patent application with the application number 11165566.8 (Symrise)), which with respect to these extracts form part of this application by reference, umami compounds as described in WO 2008/046895 A1 and EP 1 989 944 A1, which in each case with respect to these compounds form part of this application by reference and umami compounds as described in EP 2 064 959 A1 or EP 2 135 516 A1, which with respect to the corresponding compounds disclosed therein form part of this application by reference, phyllodulcin or extracts of Hydrangea macrophylla var. Thunbergii makino and flavoring compositions derived therefrom, as described in EP 2 298 084 A1 or US 2011/0076239 A1, which with respect to these extracts or phyllodulcin form part of this application by reference, hydroxyflavan derivatives and flavoring compositions derived therefrom, as described in US 2010/0292175 A1, which with respect to these compounds and the flavoring compositions derived therefrom form part of this application by reference and certain neoflavonoids as disclosed in the European patent application with the application number EP 11 181 504.9 (Symrise).

If a preparation according to the invention for example contains a comparatively high concentration of a compound of formula (I) to be used according to the invention, of a physiologically acceptable salt of a compound of formula (I), or of a mixture to be used according to the invention, it may happen that as well as the desired sensory effects described, additional undesirable taste impressions arise. These undesirable taste impressions can be at least partially reduced or even completely suppressed with flavor correctants. In such a case, the flavor correctants are preferably selected from the group consisting of sodium salts (thereby preferably sodium chloride, sodium lactate, sodium citrate, sodium acetate, sodium gluconoate), homoeriodictyol or its sodium salts, eriodictyol, trans-pellitorin and Rubus extracts, preferably Rubus extracts as described in the European patent application with the application number 11165566.8 (Symrise).

EXAMPLES

The following examples have the purpose of clarifying the invention, without limiting it thereby. Unless stated otherwise, all data refer to weight.

The extract of Mycetia balansae and the compounds balansin A and balansin B used hereunder were obtained as described in the European patent application with the application number 11168468.4 (Symrise).

Examples

The examples have the purpose of clarifying the invention, without limiting it. Unless stated otherwise, all data refer to weight.

Example 1

(4S)-7-Methoxy-4-(4-methoxyphenyl)chroman-2-one (1) and (4R)-7-methoxy-4-(4-methoxyphenyl)chroman-2-one (2)

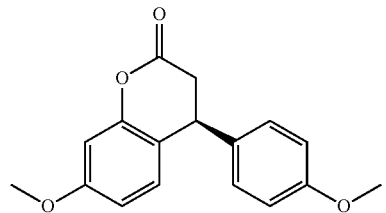

(1)

-continued (2)

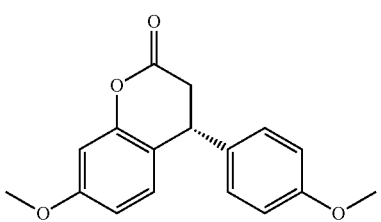

30 mmol of 3-methoxyphenol and 30 mmol of 4-methoxycinnamic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of 5% sodium bicarbonate solution, dried over sodium sulfate and concentrated by evaporation. The solid obtained was recrystallized from hexane/acetone (80:45).

Yield: 4.2 mmol (14% of theor.)
Analysis Data:
$^1$H-NMR (400 MHz, CDCl$_3$): 2.95 (dd, J=8.0/15.8 Hz, 1H); 3.03 (dd, J=5.9/15.8 Hz, 1H); 3.79 (s, 3H); 3.80 (s, 3H); 4.24 (dd, J=5.9/8.0 Hz, 1H); 6.63 (dd, J=2.6/8.5 Hz 1H); 6.68 (d, J=2.6 Hz, 1H); 6.84-6.90 (kB, 3H); 7.04-7.09 (m, 2H) ppm.
$^{13}$C-NMR (100 MHz, CDCl$_3$): 37.5 (CH$_2$); 39.3 (CH); 55.3 (CH$_3$); 55.6 (CH$_3$); 102.5 (CH); 110.7 (CH); 114.5 (CH); 118.1 (C); 128.6 (CH); 128.9 (CH); 132.7 (C); 152.4 (C); 158.9 (C); 160.0 (C); 167.8 (C=O) ppm.
Mass spectrum (EI): m/z (%)=285 (19); 284 (M$^{•+}$, 100); 256 (29); 253 (9); 242 (17); 241 (84); 227 (16); 212 (11); 211 (56); 128 (12).

Example 2

(4S)-5,7-Dimethoxy-4-(4-methoxyphenyl)chroman-2-one (3) and (4R)-5,7-dimethoxy-4-(4-methoxyphenyl)chroman-2-one (4)

(3)

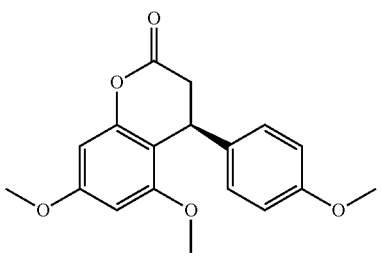

(4)

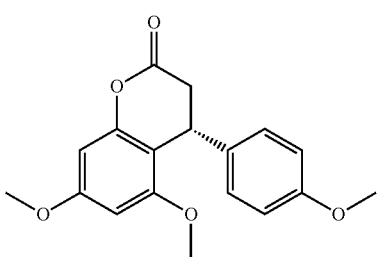

30 mmol of 3,5-dimethoxyphenol and 30 mmol of 4-methoxycinnamic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of 5% sodium bicarbonate solution, dried over sodium sulfate and concentrated by evaporation. The solid obtained was recrystallized from hexane/acetone (5:2).

Yield: 12.0 mmol (40% of theor.)
Analysis Data:
$^1$H-NMR (400 MHz, CDCl$_3$): 2.98 (m, 2H); 3.75 (s, 6H); 3.81 (s, 3H); 4.51 (t, J=4.4 Hz, 1H); 6.27 (d, J=6.3 Hz, 1H); 6.32 (d, J=6.3 Hz, 1H); 6.79 (m, 2H); 7.02 (m, 2H) ppm.
$^{13}$C-NMR (100 MHz, CDCl$_3$): 33.7 (CH); 37.3 (CH$_2$); 55.2 (CH$_3$); 55.6 (CH$_3$); 55.8 (CH$_3$); 93.9 (CH); 95.1 (CH); 106.4 (C); 114.2 (CH); 127.8 (CH); 133.6 (C); 153.0 (C); 157.4 (C); 158.6 (C); 160.6 (C); 167.8 (C=O) ppm.
Mass spectrum (EI): m/z (%)=315 (20); 314 (M$^{•+}$, 100); 286 (38); 272 (14); 271 (74); 257 (14); 241 (32); 207 (19); 121 (11); 69 (8).

Example 3

(4S)-4-(4-Hydroxyphenyl)-5,7-dimethoxy-chroman-2-one (5) and (4R)-4-(4-hydroxyphenyl)-5,7-dimethoxy-chroman-2-one (6)

(5)

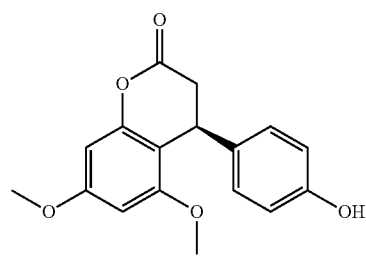

(6)

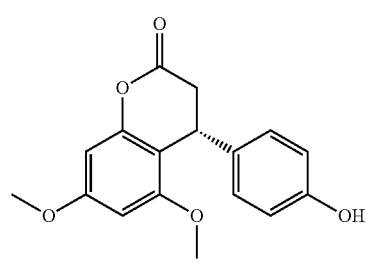

40 mmol of 3,5-dimethoxyphenol and 40 mmol of 4-hydroxycinnamic acid were put in 70 ml of 1,4-dioxane and 1.5 ml of concentrated sulfuric acid and heated under reflux for 24 hours. The reaction mixture was poured into 600 ml of water, whereupon the product precipitates. The solid is filtered off and washed with ethanol/water (1:1) and then recrystallized twice from ethanol/water (1:1).

Yield: 13.6 mmol (34% of theor.)
Analysis Data:
$^1$H-NMR (400 MHz, CDCl$_3$): 2.97 (m, 2H); 3.76 (s, 3H); 3.82 (s, 3H); 4.50 (t, J=4.6 Hz, 1H); 4.87 (s, 1H); 6.28 (d, J=2.3 Hz, 1H); 6.32 (d, J=2.3 Hz, 1H); 6.71 (m, 2H); 7.97 (m, 2H) ppm.
$^{13}$C-NMR (100 MHz, CDCl$_3$): 33.7 (CH); 37.3 (CH$_2$); 55.6 (CH$_3$); 55.8 (CH$_3$); 94.0 (CH); 95.2 (CH); 106.4 (C);

115.6 (CH); 128.0 (CH); 133.7 (C); 153.0 (C); 154.6 (C); 157.4 (C); 160.6 (C); 168.0 (C=O) ppm.

Mass spectrum (EI): m/z (%)=301 (19); 300 (M·+, 100); 272 (37); 258 (14); 257 (72); 241 (20); 207 (12); 154 (9); 153 (8); 69 (11).

Mass spectrum (EI): m/z (%)=301 (23); 300 (M·+, 100); 282 (23); 267 (25); 257 (90); 243 (31); 241 (83); 227 (41); 176 (70); 133 (27).

Example 4

(4S)-4-(3-Hydroxy-4-methoxyphenyl)-7-methoxy-chroman-2-one (7) and (4R)-4-(3-hydroxy-4-methoxyphenyl)-7-methoxy-chroman-2-one (8)

Example 5

(4S)-4-(3-Hydroxy-4-methoxyphenyl)-5,7-dimethoxy-chroman-2-one (9) and (4R)-4-(3-hydroxy-4-methoxyphenyl)-5,7-dimethoxy-chroman-2-one (10)

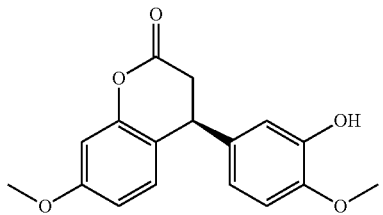

(7)

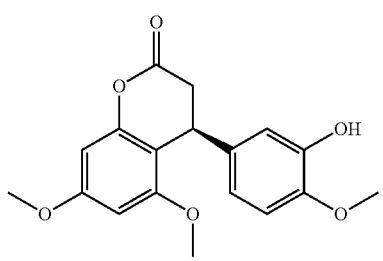

(9)

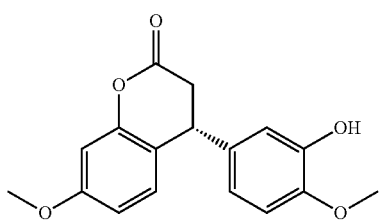

(8)

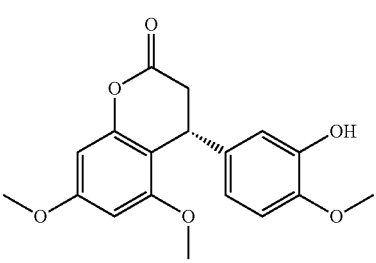

(10)

40 mmol of 3-methoxyphenol and 40 mmol of isoferulic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of 5% sodium bicarbonate solution, dried over sodium sulfate and concentrated by evaporation. The oily product was purified by column chromatography (methyl tert-butyl ether/hexane, 1:1) and the resultant solid was recrystallized from ethanol/water (1:1).

Yield: 4.1 mmol (10% of theor.)

Analysis Data:

$^1$H-NMR (400 MHz, CDCl$_3$): 2.94 (dd, J=7.7/15.8 Hz, 1H); 3.02 (dd, J=5.9/15.8 Hz, 1H); 3.80 (s, 3H); 3.86 (s, 3H); 4.18 (m, 1H); 5.70 (s, 1H); 6.59-6.67 (kB, 3H); 6.71 (d, J=2.2 Hz, 1H); 6.79 (d, J=8.3 Hz, 1H); 6.89 (m, 1H) ppm.

$^{13}$C-NMR (100 MHz, CDCl$_3$): 37.4 (CH); 39.5 (CH$_2$); 55.6 (CH$_3$); 56.0 (CH$_3$); 102.5 (CH); 110.7 (CH); 111.0 (CH); 113.7 (CH); 117.8 (C); 119.0 (CH); 128.9 (CH); 133.9 (C); 145.9 (C); 146.0 (C); 152.4 (C); 159.9 (C); 167.8 (O=O) ppm.

40 mmol of 3,5-dimethoxyphenol and 40 mmol of isoferulic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of 5% sodium bicarbonate solution, dried over sodium sulfate and concentrated by evaporation. The solid obtained was recrystallized from hexane/acetone (5:2).

Yield: 7.1 mmol (18% of theor.)

Analysis Data:

$^1$H-NMR (400 MHz, CDCl$_3$): 2.94 (dd, J=5.7/15.8 Hz, 1H); 2.99 (dd, J=3.4/15.8 Hz, 1H); 3.75 (s, 3H); 3.81 (s, 3H); 3.83 (s, 3H); 4.47 (dd, J=3.2/5.7 Hz, 1H); 5.55 (s, 1H); 6.27 (d, J=2.3 Hz, 1H); 6.31 (d, J=2.3 Hz, 1H); 6.56 (ddd, J=0.6/2.2/8.3 Hz, 1H); 6.70 (dd, J=0.3/2.2 Hz, 1H); 6.72 (d, J=8.4 Hz, 1H) ppm.

$^{13}$C-NMR (100 MHz, CDCl$_3$): 33.9 (CH); 37.3 (CH$_2$); 55.6 (CH$_3$); 55.85 (CH$_3$); 55.93 (CH$_3$); 94.0 (CH); 95.1 (CH); 106.2 (C); 110.9 (CH); 113.4 (CH); 117.9 (CH); 134.8 (C); 145.6 (C); 145.7 (O); 153.1 (C); 157.4 (C); 160.6 (C); 167.7 (C=O) ppm.

Mass spectrum (EI): m/z (%)=331 (20); 330 (M·+, 100); 302 (10); 287 (41); 273 (12); 271 (17); 257 (10); 207 (11); 176 (30); 154 (38); 137 (11).

Example 6

(4S)-4-(4-Hydroxyphenyl)-7-propoxy-chroman-2-one (11) and (4R)-4-(4-hydroxyphenyl)-7-propoxy-chroman-2-one (12)

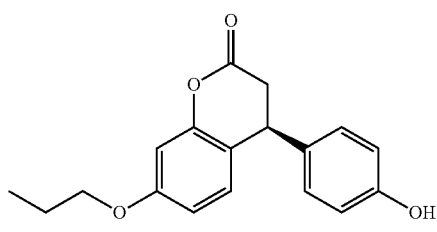

(11)

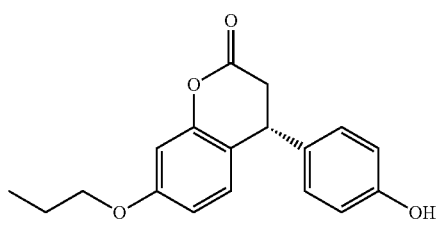

(12)

15 mmol of 3-propoxyphenol and 15 mmol of 4-hydroxycinnamic acid were put in 70 ml of 1,4-dioxane and 1.0 ml of concentrated sulfuric acid and heated under reflux for 24 hours. The reaction mixture was poured into 250 ml of 5% sodium bicarbonate solution and was extracted with 300 ml of methyl tert-butyl ether. The organic phase is then washed again with 50 ml of saturated sodium chloride solution, dried over sodium sulfate and concentrated by evaporation. The oily product was purified by column chromatography (methyl tert-butyl ether/hexane, 1:1).

Yield: 4.3 mmol (29% of theor.)

Analysis Data:

$^1$H-NMR (400 MHz, CDCl$_3$): 1.03 (t, J=7.4 Hz, 3H); 1.81 (tq, J=6.6/7.4 Hz, 2H); 2.95 (dd, J=7.6/15.7 Hz, 1H); 3.03 (dd, J=5.9/15.7 Hz, 1H); 3.90 (t, J=6.6 Hz, 2H); 4.22 (dd, J=6.1/7.5 Hz, 1H); 5.12 (bs, 1H); 6.63 (dd, J=2.5/8.4 Hz, 1H); 6.66 (d, J=2.5 Hz, 1H); 6.78 (m, 2H); 6.86 (ddd, J=0.4/0.9/8.4 Hz, 1H); 7.0 (m, 2H) ppm.

$^{13}$C-NMR (100 MHz, CDCl$_3$): 10.5 (CH$_3$); 22.5 (CH$_2$); 37.6 (CH$_2$); 39.3 (CH); 69.9 (CH$_2$); 103.0 (CH); 111.3 (CH); 115.9 (CH); 117.7 (C); 128.7 (CH); 128.8 (C); 132.9 (C); 152.3 (C); 155.0 (C); 159.5 (C); 168.1 (C=O) ppm.

Mass spectrum (EI): m/z (%)=299 (19); 298 (M·+, 100); 270 (13); 256 (25); 255 (51); 239 (17); 228 (25); 214 (11); 213 (39); 197 (15).

Example 7

(4S)-7-Ethoxy-4-(4-hydroxyphenyl)chroman-2-one (13) and (4R)-7-ethoxy-4-(4-hydroxyphenyl)chroman-2-one (14)

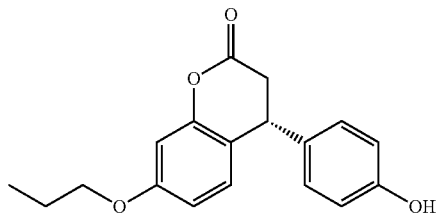

(13)

(14)

15 mmol of 3-ethoxyphenol and 15 mmol of 4-hydroxycinnamic acid were put in 70 ml of 1,4-dioxane and 1.0 ml of concentrated sulfuric acid and heated under reflux for 24 hours. The reaction mixture was poured into 250 ml of 5% sodium bicarbonate solution and was extracted with 300 ml of methyl tert-butyl ether. The organic phase is then washed again with 50 ml of saturated sodium chloride solution, dried over sodium sulfate and concentrated by evaporation. The oily product was purified by column chromatography (methyl tert-butyl ether/hexane, 1:1).

Yield: 4.5 mmol (30% of theor.)

Analysis Data:

$^1$H-NMR (400 MHz, CDCl$_3$): 1.42 (t, J=7.0 Hz, 3H); 2.94 (dd, J=7.8/15.8 Hz, 1H); 3.03 (dd, J=5.9/15.8 Hz, 1H); 4.02 (q, J=7.0 Hz, 2H); 4.22 (dd, J=5.9/7.9 Hz, 1H); 4.87 (s, 1H); 6.62 (dd, J=2.5/8.4 Hz, 1H); 6.67 (d, J=2.6 Hz, 1H); 6.79 (m, 2H); 6.86 (ddd, J=0.4/0.9/8.4 Hz, 1H); 7.01 (m, 2H) ppm.

$^{13}$C-NMR (100 MHz, CDCl$_3$): 14.7 (CH$_3$); 37.6 (CH$_2$); 39.3 (CH); 63.9 (CH$_2$); 103.0 (CH); 111.3 (CH); 115.9 (CH); 117.8 (C); 128.78 (CH); 128.81 (CH); 133.0 (C); 152.4 (C); 154.9 (C); 159.3 (C); 167.9 (C=O) ppm.

Mass spectrum (EI): m/z (%)=285 (19); 284 (M·+, 100); 256 (26); 242 (16); 241 (74); 227 (8); 225 (23); 213 (21); 128 (9); 77 (8).

Example 8

(4S)-4-(4-Hydroxy-3-methoxyphenyl)-7-methoxy-chroman-2-one (15) and (4R)-4-(4-hydroxy-3-methoxyphenyl)-7-methoxy-chroman-2-one (16)

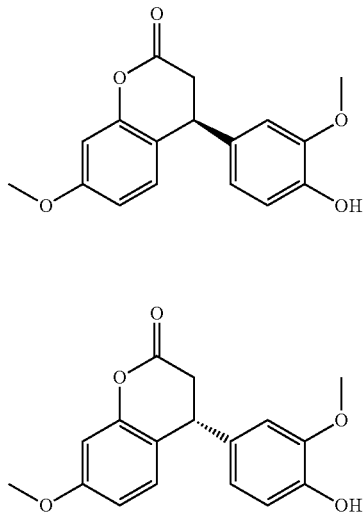

(15)

(16)

40 mmol of 3-methoxyphenol and 40 mmol of ferulic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of saturated sodium bicarbonate solution, dried over sodium sulfate and concentrated by evaporation. The crude product was purified by column chromatography (methyl tert-butyl ether/hexane, 1:1).

Yield: 12.7 mmol (32% of theor.)

Analysis Data:

$^1$H-NMR (400 MHz, CDCl$_3$): 2.95 (dd, J=8.1/15.6 Hz, 1H); 3.04 (dd, J=5.9/15.6 Hz, 1H); 3.81 (s, 3H); 3.84 (d, J=0.2 Hz, 3H); 4.21 (dd, J=5.9/8.2 Hz, 1H); 5.57 (d, J=0.3 Hz, 1H); 6.61-6.69 (kB, 4H); 6.88 (d, J=8.1 Hz, 1H); 6.89 (ddd, J=0.3/0.8/8.4 Hz, 1H) ppm.

$^{13}$C-NMR (100 MHz, CDCl$_3$): 37.6 (CH$_2$); 39.9 (CH); 55.6 (CH$_3$); 55.9 (CH$_3$); 102.5 (CH); 109.7 (CH); 110.7 (CH); 114.8 (CH); 118.0 (C); 120.5 (CH); 128.9 (CH); 132.6 (C); 145.0 (C); 146.9 (C); 152.4 (C); 160.0 (C); 167.8 (C=O) ppm.

Mass spectrum (EI): m/z (%)=301 (20); 300 (M·+, 100); 272 (11); 267 (11); 257 (46); 243 (9); 242 (13); 241 (29); 227 (22); 176 (19).

Example 9

(4S)-4-(4-Hydroxy-3-methoxyphenyl)-5,7-dimethoxy-chroman-2-one (17) and (4R)-4-(4-hydroxy-3-methoxyphenyl)-5,7-dimethoxy-chroman-2-one (18)

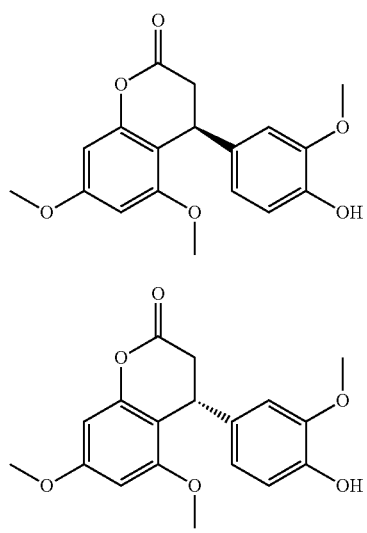

(17)

(18)

40 mmol of 3,5-dimethoxyphenol and 40 mmol of ferulic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of 5% sodium bicarbonate solution, dried over sodium sulfate and concentrated by evaporation. The solid obtained was recrystallized from methyl tert-butyl ether/hexane.

Yield: 17.4 mmol (44% of theor.)

Analysis Data:

$^1$H-NMR (400 MHz, CDCl$_3$): 2.97 (m, 2H); 3.76 (s, 3H); 3.81 (s, 3H); 3.83 (s, 3H); 4.49 (dd, J=4.5/5.3 Hz, 1H); 5.50 (d, J=0.4 Hz, 1H); 6.28 (d, J=2.3 Hz, 1H); 6.32 (d, J=2.3 Hz, 1H); 6.59 (m, 1H); 6.62 (d, J=2.1 Hz, 1H); 6.78 (d, J=8.1 Hz, 1H) ppm.

$^{13}$C-NMR (100 MHz, CDCl$_3$): 34.2 (CH); 37.4 (CH$_2$); 55.6 (CH$_3$); 55.82 (CH$_3$); 55.85 (CH$_3$); 94.0 (CH); 95.1 (CH); 106.4 (C); 109.2 (CH); 114.5 (CH); 119.5 (CH); 133.5 (C); 144.7 (C); 146.7 (C); 153.0 (C); 157.4 (C); 160.6 (C); 167.9 (C=O) ppm.

Mass spectrum (EI): m/z (%)=331 (20); 330 (M·+, 100); 302 (16); 287 (41); 272 (10); 271 (17); 257 (14); 207 (10); 176 (20); 154 (25).

Example 10

(4S)-4-(4-Hydroxyphenyl)-7-methoxy-chroman-2-one (19) and (4R)-4-(4-hydroxyphenyl)-7-methoxy-chroman-2-one (20)

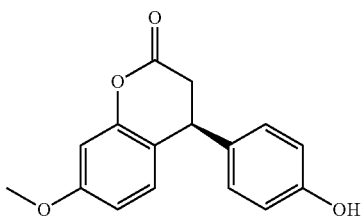

(19)

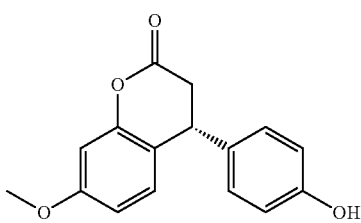

(20)

40 mmol of 3-methoxyphenol and 40 mmol of 4-hydroxycinnamic acid were put in 70 ml of 1,4-dioxane and 2.0 ml of concentrated sulfuric acid and heated under reflux for 24 hours. The reaction mixture was poured into 600 ml of 5% sodium bicarbonate solution and was extracted with 300 ml of methyl tert-butyl ether. The organic phase is then washed again with 100 ml of 5% sodium bicarbonate solution, dried over sodium sulfate and concentrated by evaporation. The solid obtained was recrystallized from hexane/acetone.

Yield: 4.4 mmol (11% of theor.)

Analysis Data:

$^1$H-NMR (400 MHz, CDCl$_3$): 2.95 (dd, J=7.8/15.7 Hz, 1H); 3.03 (dd, J=6.0/15.7 Hz, 1H); 3.80 (s, 3H); 4.23 (dd, J=6.2/7.3 Hz, 1H); 4.89 (bs, 1H); 6.64 (dd, J=2.3/8.3 Hz, 1H); 6.68 (d, J=2.7 Hz, 1H); 6.79 (m, 2H); 6.87 (ddd, J=0.3/0.8/8.8 Hz, 1H); 7.01 (m, 2H) ppm.

$^{13}$C-NMR (100 MHz, CDCl$_3$): 37.5 (CH$_2$); 39.3 (CH); 55.6 (CH$_3$); 102.5 (CH); 110.8 (CH); 115.9 (CH); 117.9 (C); 128.8 (CH); 128.9 (CH); 132.9 (C); 152.4 (C); 154.9 (C); 160.0 (C); 167.9 (C=O) ppm.

Mass spectrum (EI): m/z (%)=271 (18); 270 (M·+, 100); 242 (29); 228 (20); 227 (97); 212 (9); 211 (37); 128 (9); 121 (9); 77 (10).

Example 11

(4S)-4-(4-Hydroxy-3-methoxyphenyl)-7-propoxy-chroman-2-one (21) and (4R)-4-(4-hydroxy-3-methoxyphenyl)-7-propoxy-chroman-2-one (22)

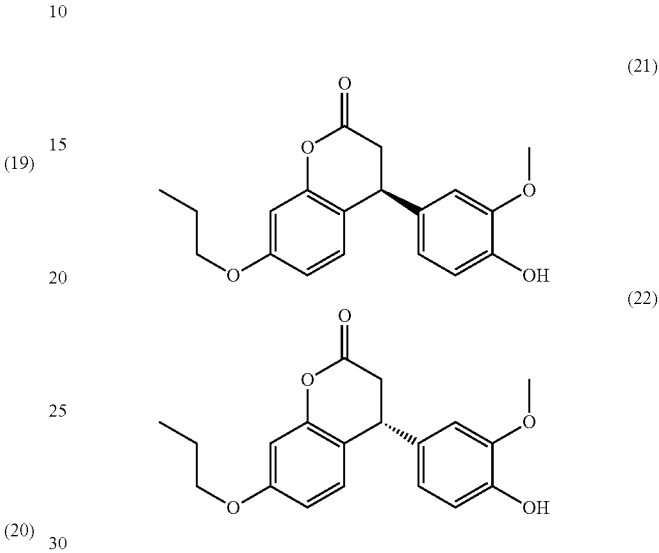

15 mmol of 3-propoxyphenol and 15 mmol of ferulic acid were put in 70 ml of 1,4-dioxane and 1.0 ml of concentrated sulfuric acid and heated under reflux for 24 hours. The reaction mixture was poured into 250 ml of saturated sodium bicarbonate solution and extracted with 300 ml of methyl tert-butyl ether. The organic phase is then washed with 50 ml of saturated sodium chloride solution, dried over sodium sulfate and concentrated by evaporation. The crude product was purified by column chromatography (methyl tert-butyl ether/hexane, 1:1).

Yield: 7.0 mmol (47% of theor.)

Analysis Data:

$^1$H-NMR (400 MHz, CDCl$_3$): 1.04 (t, J=7.4 Hz, 3H); 1.81 (tq, J=6.5/7.4 Hz, 2H); 2.95 (dd, J=8.1/15.8 Hz, 1H); 3.04 (dd, J=5.9/15.8 Hz, 1H); 3.83 (s, 3H); 3.91 (t, J=6.6 Hz, 2H); 4.21 (dd, J=5.8/8.2 Hz, 1H); 5.59 (d, J=0.3 Hz, 1H); 6.61-6.68 (m, 4H); 6.87 (ddd, J=0.4/0.9/8.4 Hz, 1H); 6.87 (d, J=8.1 Hz, 1H) ppm.

$^{13}$C-NMR (100 MHz, CDCl$_3$): 10.5 (CH$_3$); 22.5 (CH$_2$); 37.6 (CH$_2$); 39.9 (CH); 55.9 (CH$_3$); 69.9 (CH$_2$); 103.0 (CH); 109.7 (CH); 111.3 (CH); 114.8 (CH); 117.7 (C); 120.5 (CH); 128.8 (CH); 132.6 (C); 145.0 (C); 146.9 (C); 152.4 (C); 159.5 (C); 167.9 (C=O) ppm.

Mass spectrum (EI): m/z (%)=329 (22); 328 (M·+, 100); 286 (15); 285 (32); 269 (20); 255 (11); 243 (18); 227 (10); 213 (11); 176 (13).

Example 12

(4S)-5-Hydroxy-4-(4-hydroxy-3-methoxyphenyl)-7-methoxy-chroman-2-one (23) and (4R)-5-hydroxy-4-(4-hydroxy-3-methoxyphenyl)-7-methoxy-chroman-2-one (24) plus (4S)-7-hydroxy-4-(4-hydroxy-3-methoxyphenyl)-5-methoxy-chroman-2-one (A) and (4R)-7-hydroxy-4-(4-hydroxy-3-methoxyphenyl)-5-methoxy-chroman-2-one (B)

0.5 ml of concentrated sulfuric acid was added to a mixture of 17.5 mmol of trans-4-hydroxycinnamic acid and 17.5 mmol of 5-methylresorcinol in 40 ml of 1,4-dioxane and it was heated under reflux for 12 hours. After cooling, the reaction mixture was poured into 250 ml of demineralized water and was extracted with 150 ml of ethyl acetate (EAc). The organic phase was washed twice with 50 ml of demineralized water and 50 ml of 5% sodium bicarbonate solution each time, and was dried over sodium sulfate. After removing the solvent, the product was purified by silica-gel column chromatography (solvent: ethyl acetate/hexane 2:3). According to NMR, the product consisted of two isomers, which were in the ratio 37:63 (23/24:A/B). Further separation was carried out by preparative HPLC (Phenomenex Luna C18 (2), 5 μm, 150×21.5 mm; acetonitrile/water 75:25; 25 ml/min; 105 bar).

Yield: 9.8 mmol (56% of theor.)

Example 12a (4S)-5-Hydroxy-4-(4-hydroxy-3-methoxyphenyl)-7-methoxy-chroman-2-one (23) and (4R)-5-hydroxy-4-(4-hydroxy-3-methoxyphenyl)-7-methoxy-chroman-2-one (24)

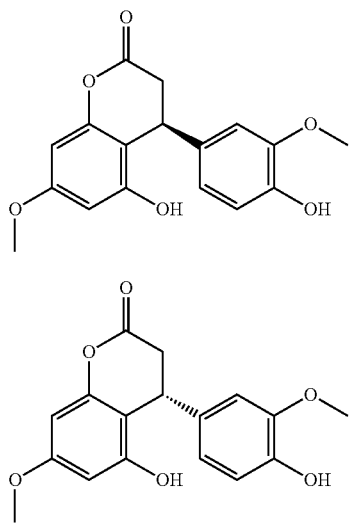

Analysis Data:

Retention time: 20.3 min-21.8 min $^1$H-NMR (400 MHz, CDCl$_3$): 2.97 (dd, J=3.6/15.8 Hz; 1H); 3.03 (dd, J=6.1/15.8 Hz; 1H); 3.79 (s, 3H); 3.82 (s, 3H); 4.44 (dd, J=3.6/6.1 Hz, 1H); 4.96 (bs, 1H); 5.53 (bs, 1H); 6.21 (d, J=2.3 Hz, 1H); 6.35 (d, J=2.3 Hz, 1H); 6.62 (d, J=2.0 Hz; 1H); 6.64 (dd, J=2.0/8.6 Hz, 1H); 6.82 (d, J=8.6 Hz, 1H) ppm.

$^{13}$C-NMR (100 MHz, (CD$_3$)$_2$SO): 33.2 (CH); 37.1 (CH$_2$); 55.1 (CH$_3$); 55.5 (CH$_3$); 93.0 (CH); 97.5 (CH); 105.2 (C); 111.3 (CH); 115.2 (CH); 118.2 (CH); 132.7 (C); 145.3 (C); 147.5 (C); 154.0 (C); 155.3 (C); 159.5 (C); 167.8 (C=O) ppm.

HRMS [M-H; C$_{17}$H$_{15}$O$_6$]: calc.: 315.0874. found: 315.0902.

Example 12b (4S)-7-Hydroxy-4-(4-hydroxy-3-methoxyphenyl)-5-methoxy-chroman-2-one (A) and (4R)-7-hydroxy-4-(4-hydroxy-3-methoxyphenyl)-5-methoxy-chroman-2-one (B)

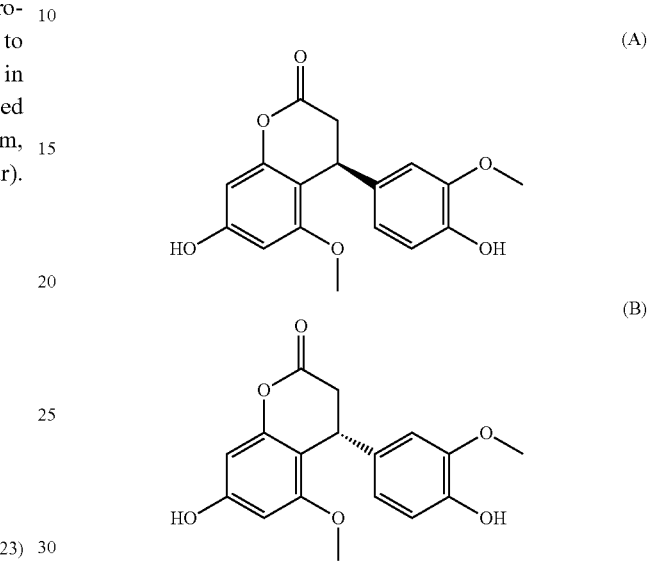

Analysis Data:

Retention time: 17.0 min-19.8 min $^1$H-NMR (400 MHz, CDCl$_3$): 2.95-2.99 (kB, 2H); 3.76 (s, 3H); 3.81 (s, 3H); 4.48 (dd, J=3.9/4.7 Hz, 1H); 5.19 (bs, 1H); 5.49 (bs, 1H); 6.25 (d, J=2.3 Hz, 1H); 6.27 (d, J=2.3 Hz, 1H); 6.59 (dd, J=2.1/7.9 Hz; 1H); 6.61 (d, J=2.1 Hz, 1H); 6.79 (d, J=7.9 Hz, 1H) ppm.

$^{13}$C-NMR (100 MHz, (CD$_3$)$_2$SO): 33.1 (CH); 38.8-40.1 (CH$_2$; masked by solvent signal); 55.5 (CH$_3$); 55.6 (CH$_3$); 95.4 (CH); 95.6 (CH); 104.3 (C); 111.1 (CH); 115.2 (CH); 118.1 (CH); 132.7 (C); 145.3 (C); 147.5 (C); 152.5 (C); 157.0 (C); 158.2 (C); 167.7 (C=O) ppm.

HRMS [M-H; C$_{17}$H$_{15}$O$_6$]: calc.: 315.0874. found: 315.0920.

Example 13

(4S)-7-Ethoxy-4-(4-hydroxy-3-methoxyphenyl)chroman-2-one (25) and (4R)-7-ethoxy-4-(4-hydroxy-3-methoxyphenyl)chroman-2-one (26)

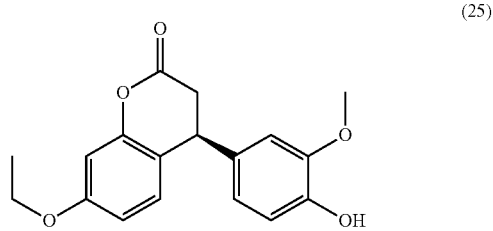

-continued

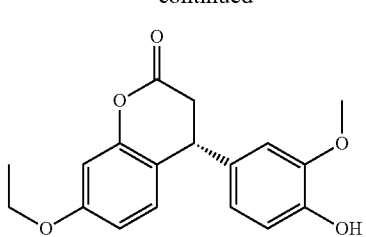

(26)

15 mmol of 3-ethoxyphenol and 15 mmol of ferulic acid were put in 70 ml of 1,4-dioxane and 1.0 ml of concentrated sulfuric acid and heated under reflux for 24 hours. The reaction mixture was poured into 250 ml of saturated sodium bicarbonate solution and extracted with 300 ml of methyl tert-butyl ether. The organic phase is then washed with 50 ml of saturated sodium chloride solution, dried over sodium sulfate and concentrated by evaporation. The crude product was purified by column chromatography (methyl tert-butyl ether/hexane, 1:1).

Yield: 4.3 mmol (29% of theor.)

Analysis Data:

$^1$H-NMR (400 MHz, CDCl$_3$): 1.42 (t, J=7.0 Hz, 3H); 2.95 (dd, J=5.9/15.6 Hz, 1H); 3.04 (dd, J=5.9/15.6 Hz, 1H); 3.83 (s, 3H); 4.01 (q, J=7.0 Hz, 2H); 4.21 (dd, J=5.8/8.1 Hz, 1H); 5.60 (bs, 1H); 6.61-6.67 (m, 4H); 6.87 (ddd, J=0.4/0.9/8.4 Hz, 1H); 6.87 (d, J=8.0 Hz, 1H) ppm.

$^{13}$C-NMR (100 MHz, CDCl$_3$): 14.7 (CH$_3$); 37.6 (CH$_2$); 39.9 (CH); 55.9 (CH$_3$); 63.8 (CH$_2$); 103.0 (CH); 109.7 (CH); 111.2 (CH); 114.8 (CH); 117.8 (C); 120.5 (CH); 128.8 (CH); 132.6 (C); 145.0 (C); 146.9 (C); 152.4 (C); 159.3 (C); 167.9 (C=O) ppm.

Mass spectrum (EI): m/z (%)=315 (20); 314 (M$^{\cdot+}$, 100); 286 (11); 272 (8); 271 (39); 257 (11); 255 (22); 243 (10); 241 (14); 176 (11).

Practical Example 1

Investigations of Intensification of the Impression of Sweetness or Masking of Bitterness Practical Example 1a Intensification of the Impression of Sweetness of a Sugar Solution For quantifying the intensification of the impression of sweetness, the sweetness of a 5 wt % sucrose solution (consisting of 5 wt % sucrose in water) and of a sample that consisted of water, 5 wt % sucrose and a specified amount (i.e. that given below in each case) of test substance was determined by a panel of experts. The assessment was based on a scale from 1 [not sweet] to 10 [extremely sweet]. The intensification of the impression of sweetness (in %) was calculated from the respective mean values of the assessments of the sucrose solution and of the respective sample to be investigated containing the test substance. The test substances used were in each case a racemic mixture of the following compounds to be used according to the invention.

| Substance | Impression of sweetness (1-10) without | with | % intensification of the impression of sweetness |
|---|---|---|---|
| (1) + (2), ratio 1:1, 50 ppm | 4.8 ± 0.9 | 5.4 ± 0.9 | 12% (p < 0.08) |
| (11) + (12), ratio 1:1, 25 ppm | 5.8 ± 1.1 | 6.6 ± 1.5 | 14% (p < 0.09) |
| (15) + (16), ratio 1:1, 50 ppm | 5.2 ± 0.9 | 6.7 ± 1.4 | 29% (p < 0.001) |
| (17) + (18), ratio 1:1, 50 ppm | 4.2 ± 1.4 | 7.1 ± 1.8 | 37% (p < 0.002) |
| (19) + (20), ratio 1:1, 50 ppm | 4.7 ± 1.1 | 5.4 ± 1.1 | 14% (p < 0.09) |
| (23) + (24), ratio 1:1, 50 ppm | 4.2 ± 0.8 | 7.6 ± 1.5 | 47% (p < 0.00001) |

Practical Example 1a-1

Intensification of the Impression of Sweetness of a Sugar Solution

In order to quantify the intensification of the impression of sweetness, the sweetness of a 5 wt % sucrose solution (consisting of 5 wt % sucrose in water) and of a sample that consisted of water, 5 wt % sucrose and a specified amount (i.e. given below in each case) of test substance, was determined by a panel of experts. The assessment was based on a scale from 1 [not sweet] through 10 [extremely sweet]. The intensification of the impression of sweetness (in %) was calculated from the respective mean values of the assessments of the sucrose solution and of the respective sample to be investigated containing the test substance.

| Substance | Impression of sweetness (1-10) without | with | % intensification of the impression of sweetness |
|---|---|---|---|
| (23) + (24), ratio 1:1, 50 ppm | 4.2 ± 0.8 | 7.6 ± 1.5 | 47% (p < 0.00001) |
| (A) + (B), ratio 1:1, 50 ppm | 5.4 ± 1.6 | 5.8 ± 1.4 | 8% (p < 0.5) |
| Mixture according to Example 12 consisting of: (23) + (24), ratio 1:1, 37 ppm (A) + (B), ratio 1:1, 63 ppm | 5.1 ± 1.5 | 7.4 ± 1.5 | 44% (p < 0.0002) |

This example clearly shows that structurally similar compounds with a corresponding residue at position C5 (e.g. compounds (A) and (B)) instead of position C7 (e.g. compounds (23) and (24)) have a much lower sweetness intensifying action than compounds to be used according to the invention.

Practical Example 1b

Reduction of Bitterness of a Solution of Bitter Substance

To quantify the reduction (i.e. the masking or decrease) of the impression of bitterness in a sample, the bitterness of a solution containing 500 ppm caffeine or 100 ppm naringin was compared by a panel of experts, in each case against a sample that contained 500 ppm caffeine or 100 ppm naringin and additionally the amount stated in each case of a substance to be assessed (with respect to capacity for reducing bitterness) (assessment scale: 1 [not bitter] through 10 [extremely bitter]). Evaluation, i.e. calculation of the reduction (in %) of the impression of bitterness, was based in each case on the mean values of the assessment of the panel of experts.

| Test substance | Bitter substance | Impression of bitterness (1-10) without | Impression of bitterness (1-10) with | % reduction of the impression of bitterness (significance) |
|---|---|---|---|---|
| 25 ppm (15) + (16) (ratio 1:1) | 500 ppm caffeine | 4.2 ± 1.6 | 3.2 + 1.4 | 23.7% ($p < 0.06$) |
| 50 ppm (19) + (20) (ratio 1:1) | 500 ppm caffeine | 3.9 ± 1.1 | 3.6 + 1.5 | 9.9% ($p < 0.6$) |
| 25 ppm (15) + (16) (ratio 1:1) | 100 ppm naringin | 4.1 ± 1.8 | 3.2 ± 1.9 | 20.5% ($p < 0.2$) |
| 25 ppm (17) + (18) (ratio 1:1) | 100 ppm naringin | 6.1 ± 2.2 | 4.8 ± 2.5 | 9.9% ($p < 0.2$) |

Practical Example 2

Semifinished Products

| Ingredient | A | B | C | D | E | F | G | H |
|---|---|---|---|---|---|---|---|---|
| "Liquid sugar", containing 80% sucrose | 99.85 | — | — | — | — | — | 99.80 | — |
| Compound (15) + (16) (ratio 1:1) | 0.025 | 10 | — | 9 | — | 4 | — | 7 |
| Compound (23) + (24) (ratio 1:1) | 0.025 | — | 8 | — | 10 | 5 | 0.05 | — |
| Rebaudioside A 98% | — | 80 | — | — | — | 25 | 0.01 | 68.5 |
| Stevioside 95% | — | — | 70 | — | — | — | — | — |
| Balansin A | 0.05 | 5 | — | 70 | — | 7 | 0.02 | 9 |
| Balansin B | — | 5 | 15 | — | — | 4 | — | 9 |
| Extract of *Mycetia balansae* containing 5 wt % balansin A and 5 wt % balansin B, relative to the total weight of the extract | — | — | — | 21 | — | — | — | — |
| Extract of *Rubus suavissimus*, containing 5 wt % rubusoside, relative to the total weight of the extract e.g. from PlantExtract | — | — | — | 25 | — | 25 | 0.07 | — |
| Extract of *Hydrangea dulcis* containing 8% phyllodulcin, relative to the total weight of the extract | — | — | — | 25 | — | 25 | — | — |
| Phloretin | 0.02 | — | 4 | 5 | 3.2 | 3.5 | 0.02 | 5 |
| Hesperetin | 0.02 | — | 1 | 5 | 0.8 | 1 | 0.02 | 1 |
| 3′,7-Dihydroxy-4′-methoxyflavan according to EP 2 253 226 | 0.01 | — | 2 | 8 | — | — | 0.01 | — |
| Neohesperidin dihydrochalcone | — | — | — | — | — | 0.5 | — | — |
| Homoeriodictyol, sodium salt | — | — | — | — | 16 | — | — | — |
| Vanillin, natural | — | — | — | 2 | — | — | — | — |
| Sugar distillate from cane sugar (e.g. Treatt) | — | — | — | — | — | — | — | 0.5 |

The ingredients are mixed in the proportions stated above and can then be used (further) in this form. The typical dosage of preparations A and G in the finished product is in the range from 7 through 15 wt %, relative to the total weight of the finished product. The typical dosage of the other preparations from Practical example 5 is in the range from 0.01 through 0.1 wt %, preferably 0.03 through 0.06 wt %, relative to the total weight of the finished product.

Practical Example 3

Mixtures or Semifinished Products According to the Invention

| Ingredient | A | B | C | D | E | F | G | H |
|---|---|---|---|---|---|---|---|---|
| Compound (17) + (18) (ratio 1:1) | 80 | 20 | — | 25 | — | 20 | — | 15 |
| Compound (23) + (24) (ratio 1:1) | 20 | 80 | 50 | — | 20 | 20 | 20 | 15 |
| Balansin A | — | — | — | — | 25 | — | — | 5 |
| Balansin B | — | — | — | — | — | — | — | 5 |
| Rebaudioside A 98% | — | — | 50 | 25 | — | — | — | 20 |
| Stevioside 95% | — | — | — | 25 | — | — | — | — |
| Saccharin ® sodium salt | — | — | — | — | — | 20 | — | — |
| Cyclamate ® | — | — | — | — | — | 75 | — | — |
| Acesulfame ® K | — | — | — | — | — | 20 | — | — |
| Aspartame ® | — | — | — | — | — | 20 | — | — |
| Neotame ® | — | — | — | — | 5 | — | — | — |
| Thaumatin | — | — | — | — | — | — | — | 20 |
| Sucralose ® | — | — | — | — | — | — | 80 | — |
| Glycyrrhizin ammonium salt | — | — | — | — | — | — | — | 20 |

The ingredients are mixed in the proportions stated above and used for sweetening orally consumable preparations. The typical dosage of mixtures A through H in the finished product is in the range from 0.001 through 0.5 wt %, preferably in the range from 0.003 through 0.1 wt %, relative to the total weight of the finished product.

Practical Example 4

Semifinished Products (with Calorie-Free Sugars and/or Sugar Alcohols)

| Ingredient | Preparation (amount used, wt %) | | | | | | | |
|---|---|---|---|---|---|---|---|---|
| | A | B | C | D | E | F | G | H |
| Preparation A from practical example 3 | | 0.05 | | | 0.05 | | | 0.05 |
| Preparation C from practical example 3 | | | 0.05 | | | 0.05 | | |
| Preparation H from practical example 3 | | | | 0.05 | | | 0.05 | |
| Compound (23) + (24) (ratio 1:1) | 0.05 | | | | | | | |
| Maltitol | 50 | 10 | | | | | | |
| Mannitol | | 10 | | | | | | |
| Sorbitol | 20 | 20 | | | | | | |
| Erythritol | 29.95 | 59.95 | 99.95 | 99.95 | | 50 | 50 | 99.95 |
| Xylitol | | | | | | | 49.95 | |
| Palatinose | | | | | 50 | | | |
| Tagatose | | | | | 49.95 | 49.95 | | |

The substances are mixed in the proportions stated above and used for sweetening orally consumable preparations. The typical dosage of the semifinished products A through H in the finished product is in the range from 0.01 through 80 wt %, preferably in the range from 0.1 through 50 wt %, particularly preferably in the range from 0.1 through 10 wt %, in each case relative to the total weight of the finished product. The semifinished products A through H can be used as a sweetener, e.g. also directly for coffee or tea.

Practical Example 5

Spray-Dried Preparation as Semifinished Product for Flavoring Finished Products

| Ingredient | Amount used, wt % | | | | |
|---|---|---|---|---|---|
| Preparation | A | B | C | D | E |
| Drinking water | 60.8 | 60.8 | 60.8 | 60.8 | 60.8 |
| Maltodextrin from wheat | 24.3 | 24.3 | 24.3 | 24.3 | 24.3 |
| Gum arabic | 6.1 | 6.1 | 6.1 | 6.1 | 6.1 |
| Compound (17) + (18) (ratio 1:1) | 8.8 | 3.3 | 4.0 | — | — |
| Compound (23) + (24) (ratio 1:1) | — | 3.3 | 1.5 | 3.3 | 4.4 |
| Hesperetin | — | 2.2 | — | — | 1.1 |
| Homoeriodictyol, sodium salt | — | — | — | 5.5 | 3.3 |
| Phloretin | — | — | 3.3 | — | — |

The drinking water is put in a vessel and the maltodextrin and the gum arabic are dissolved therein. Then the aromatic substances are emulsified in the carrier solution using a Turrax. The temperature of the spraying solution should not exceed 30° C. The mixture is then spray-dried (required inlet temperature: 185-195° C., required outlet temperature: 70-75° C.).

Practical Example 6

Solutions of the Semifinished Products

The mixtures and semifinished products from the above Practical examples 5, 6 and 7 can also be taken up in water, propylene glycol, glycerol or ethanol or preferably in mixtures of the aforementioned solvents (e.g. water-propylene glycol, water-glycerol, water-ethanol, glycerol-ethanol, glycerol-propylene glycol, propylene glycol-ethanol) for example as 1-20% solution, preferably 2-10%, particularly preferably 5% solution and dissolved completely by heating gently.

Practical Example 7

Reduced-Sugar Refreshing Lemon Drink

| Ingredient | Amount used, wt % | | | | | |
|---|---|---|---|---|---|---|
| Preparation | A | B | C | D | E | F |
| Sugar (sucrose) | 8 | 8 | 8 | 8 | 8 | 7 |
| Citric acid | 0.15 | 0.15 | 0.15 | 0.15 | 0.15 | 0.15 |
| Lemon flavor | 0.1 | 0.1 | 0.1 | 0.1 | 0.1 | 0.1 |
| Compound (17) + (18) (ratio 1:1) | 0.005 | — | 0.0020 | — | 0.0025 | — |
| Compound (23) + (24) (ratio 1:1) | — | 0.005 | 0.0020 | 0.0025 | — | 0.005 |
| Balansin A | — | — | — | — | 0.001 | 0.001 |
| Balansin B | — | — | — | 0.002 | — | — |

-continued

| Ingredient | Amount used, wt % | | | | | |
|---|---|---|---|---|---|---|
| Preparation | A | B | C | D | E | F |
| Phloretin | — | — | — | — | 0.001 | — |
| Hesperetin | — | — | 0.010 | — | — | — |
| 3',7-Dihydroxy-4'-methoxyflavan according to EP 2 253 226 | — | — | — | — | — | 0.0025 |
| Extract of *Rubus suavissimus*, containing 5 wt % rubusoside rel. to the total weight of the extract | — | — | — | 0.010 | — | — |
| Extract of *Hydrangea dulcis* containing 8% phyllodulcin, relative to the total weight of the extract | — | — | — | — | 0.010 | — |
| Water | to 100 | | | | | |

The ingredients were mixed in the order stated and made up to 100% with water. The mixtures are filled in glass bottles and carbonated.

Practical Example 8

Soft Drink of the "Cola" Type

| Ingredient | Preparation (amount used, wt %) | | | | | | |
|---|---|---|---|---|---|---|---|
|  | A | B | C | D | E | F | G |
| Sucrose | 0 | 8 | 7 | 7 | — | 7 | — |
| Glucose/fructose corn syrup, containing 55 wt % fructose | — | — | — | — | 8 | — | 7 |
| Aromatic composition A from practical example 2 | 10 | — | — | — | — | — | — |
| Aromatic composition B from practical example 3 | — | 0.005 | — | — | — | — | — |
| Aromatic composition C from practical example 3 | — | — | 0.0125 | — | — | — | — |
| Aromatic composition D from practical example 3 | — | — | — | 0.015 | — | — | — |
| Aromatic composition E from practical example 3 | — | — | — | — | 0.03 | — | — |
| Aromatic composition F from practical example 3 | — | — | — | — | — | 0.01 | — |
| Aromatic composition H from practical example 3 | — | — | — | — | — | — | 0.015 |
| Phosphoric acid | 0.07 | 0.07 | 0.07 | 0.07 | 0.07 | 0.07 | 0.07 |
| Citric acid | 0.06 | 0.06 | 0.06 | 0.06 | 0.06 | 0.06 | 0.06 |
| Caramel color | 0.14 | 0.14 | 0.14 | 0.14 | 0.14 | 0.14 | 0.14 |
| Caffeine | 0.01 | 0.01 | 0.01 | 0.01 | 0.01 | 0.01 | 0.01 |
| Beverage emulsion of "Cola" type | 0.05 | 0.05 | 0.05 | 0.05 | 0.05 | 0.05 | 0.05 |
| Water | to 100 | | | | | | |

The ingredients were mixed in the order stated, filled in bottles and carbonated.

Practical Example 9

Reduced-Sugar Refreshing Beverage of "Cola" Type

Preparation A: comparative preparation with 10 wt % sugar
Preparation B-G: reduced-sugar preparations according to the invention with 8 wt % sugar

| Ingredient | Preparation (amount used, wt %) | | | | | | |
|---|---|---|---|---|---|---|---|
| | A | B | C | D | E | F | G |
| Sucrose | 10 | 8 | 8 | 8 | — | — | — |
| Glucose/fructose corn syrup, containing 55 wt % fructose | — | — | — | — | 8 | 8 | 8 |
| Compound (15) + (16) (ratio 1:1) | — | — | 0.003 | 0.0025 | — | 0.003 | 0.0025 |
| Compound (23) + (24) (ratio 1:1) | — | 0.005 | — | 0.0025 | 0.005 | — | 0.0025 |
| Phosphoric acid | 0.07 | 0.07 | 0.07 | 0.07 | 0.07 | 0.07 | 0.07 |
| Citric acid | 0.06 | 0.06 | 0.06 | 0.06 | 0.06 | 0.06 | 0.06 |
| Caramel color | 0.14 | 0.14 | 0.14 | 0.14 | 0.14 | 0.14 | 0.14 |
| Caffeine | 0.01 | 0.01 | 0.01 | 0.01 | 0.01 | 0.01 | 0.01 |
| Beverage emulsion of "Cola" type | 0.05 | 0.05 | 0.05 | 0.05 | 0.05 | 0.05 | 0.05 |
| Water | fill to 100% | | | | | | |

The ingredients were mixed in the order stated and made up to 100% with water. The mixtures are filled in glass bottles and carbonated.

Practical Example 12

Chewing Gum

| Part | Ingredient | Amount used, wt % |
|---|---|---|
| A | Chewing gum base, company "Jagum T" | 30.95 |
| B | Sorbitol, powdered | 39.00 |
| | Isomalt ® (Palatinit GmbH) | 9.50 |
| | Xylitol | 2.00 |
| | Mannitol | 3.00 |
| | Aspartame ® | 0.10 |
| | Acesulfame ® K | 0.10 |
| | Emulgum ® (Colloides Naturels, Inc.) | 0.30 |
| C | Sorbitol, 70% | 14.00 |
| | Glycerol | 1.00 |
| D | Compound (23) + (24) (ratio 1:1) | 0.05 |

Parts A through D are mixed and kneaded thoroughly. The raw mixture can be processed to chewing gums ready for consumption, e.g. in the form of thin strips.

Practical Example 13

Toothpaste

| Part | Ingredient | Amount used, wt % |
|---|---|---|
| A | Demineralized water | 23.08 |
| | Sorbitol (70%) | 45.00 |
| | Solbrol ® M, sodium salt (Bayer AG, p-hydroxybenzoic acid alkyl ester) | 0.15 |
| | Trisodium phosphate | 0.10 |
| | Compound (15) + (16) (ratio 1:1) | 0.02 |
| | Sodium monofluorophosphate | 1.12 |
| | Polyethylene glycol 1500 | 5.00 |
| B | Sident 9 (abrasive silicon dioxide) | 10.00 |
| | Sident 22 S (thickening silicon dioxide) | 8.00 |
| | Sodium carboxymethylcellulose | 0.90 |
| | Titanium dioxide | 0.50 |
| C | Demineralized water | 4.53 |
| | Sodium lauryl sulfate | 1.50 |
| D | Peppermint flavor | 0.1 |

The ingredients of parts A and B are each premixed and stirred well together under vacuum at 25-30° C. for 30 min. Part C is premixed and added to A and B; D is added and the mixture is stirred well at 25-30° C. for 30 min under vacuum. After returning to normal pressure, the toothpaste is ready and can be filled.

Practical Example 14

Sugar-Free Hard Candy

| Ingredient | Content (amounts in wt %) | | | |
|---|---|---|---|---|
| | A | B | C | D |
| Palatinit, type M | 75.00 | 74.00 | 75.50 | 75.00 |
| Citric acid | — | 1.0 | 0.5 | — |
| Water | 24.885 | 24.844 | 23.88 | 24.8815 |
| Yellow dye | — | 0.01 | — | — |
| Red dye | — | — | 0.01 | — |
| Blue dye | 0.01 | — | — | 0.01 |
| Peppermint flavor | 0.1 | — | — | 0.1 |
| Lemon flavor | — | 0.1 | — | — |
| Red fruit flavor | — | — | 0.1 | — |
| Rebaudioside A 98% | — | 0.040 | — | — |
| Compound (15) + (16) (ratio 1:1) | — | — | 0.010 | 0.005 |
| Compound (23) + (24) (ratio 1:1) | 0.005 | 0.002 | — | — |
| Hesperetin | — | 0.001 | — | 0.001 |
| Phloretin | — | 0.002 | — | — |
| 3',7-Dihydroxy-4'-methoxyflavan according to EP 2 253 226 | — | — | — | 0.0025 |

Palatinit was mixed with water after optionally adding the citric acid and the mixture was melted at 165° C. and then cooled to 115° C. The flavorings and the other ingredients were added and, after thorough mixing, were poured into molds, removed from the molds after solidifying and then wrapped individually.

Practical Example 15

Reduced-Sugar Boiled Pudding

Preparation A: comparative preparation with full sugar content

Preparation B: comparative preparation with reduced sugar content

Preparation C-F: preparations according to the invention with reduced sugar content

|  | Preparation (amounts in wt %) | | | | | |
| --- | --- | --- | --- | --- | --- | --- |
| Ingredient | A | B | C | D | E | F |
| Sucrose | 7.8 | 5.4 | 5.4 | 5.4 | 5.4 | 5.4 |
| Starch | 3.0 | 3.0 | 3.0 | 3.0 | 3.0 | 3.0 |
| Skim milk powder | 1.5 | 1.5 | 1.5 | 1.5 | 1.5 | 1.5 |
| Aubygel MR50 | 0.5 | 0.5 | 0.5 | 0.5 | 0.5 | 0.5 |
| Compound (17) + (18) (ratio 1:1) | — | — | 0.01 | 0.005 | 0.005 | 0.003 |
| Extract (e.g. from PlantExtract) of *Rubus suavissimus*, containing 5 wt % rubusoside, relative to the total weight of the extract | — | — | — | — | 0.010 | 0.005 |
| Hesperetin | — | — | — | 0.001 | — | 0.001 |
| Phloretin | — | — | — | 0.002 | — | 0.001 |
| 3',7-Dihydroxy-4'-methoxyflavan according to EP 2 253 226 | — | — | — | — | — | 0.001 |
| Vanilla pod extract, spray-dried (Symrise) | 0.1 | 0.1 | 0.1 | 0.1 | 0.1 | 0.1 |
| Milk 1.5% fat | | | to 100 | | | |

The solid ingredients were assembled and stirred with the milk. The mixture was heated to 95° C. for 2 min while stirring well, filled and cooled to 5-8° C.

Practical Example 16

Low-Fat Yoghurts

Preparation A: comparative preparation with full sugar content
Preparation B-D: preparations according to the invention

|  | Preparation (amounts in wt %) | | | |
| --- | --- | --- | --- | --- |
| Ingredient | A | B | C | D |
| Sucrose | 10 | 8 | 6 | — |
| Fruit preparation, strawberry | 10 | 10 | 10 | 10 |
| Rebaudioside A 98% | — | — | — | 0.050 |
| Compound (15) + (16) (ratio 1:1) | — | — | 0.005 | 0.0075 |
| Compound (23) + (24) (ratio 1:1) | — | 0.005 | — | — |
| Extract of *Rubus suavissimus* (e.g. from PlantExtract) containing 5 wt % rubusoside, relative to the total weight of the extract | — | — | 0.010 | — |
| Hesperetin | — | 0.001 | 0.001 | 0.001 |
| Phloretin | — | — | 0.002 | — |
| Hopmoeriodictyol, sodium salt | — | — | — | 0.005 |
| Natural strawberry flavor | 0.1 | 0.1 | 0.1 | 0.1 |
| Yoghurt, 0.1% fat | | to 100 | | |

The ingredients were mixed and cooled at 5° C.

Practical Example 17

Mixed Milk Drinks

Preparation A: comparative preparation with full sugar content
Preparation B-D: preparations according to the invention

|  | Preparation (amounts in wt %) | | | |
| --- | --- | --- | --- | --- |
| Ingredient | A | B | C | D |
| Sucrose | 10 | 8 | 7 | — |
| Fructose | — | — | 0.5 | — |
| Rebaudioside A 98% | — | — | — | 0.040 |
| Compound (15) + (16) (ratio 1:1) | — | 0.005 | 0.0025 | 0.0025 |
| Balansin A | — | 0.003 | 0.001 | 0.001 |
| Extract of *Rubus suavissimus* (e.g. from PlantExtract) containing 5 wt % rubusoside, relative to the total weight of the extract | — | — | 0.010 | — |
| Hesperetin | — | 0.003 | 0.002 | 0.005 |
| Phloretin | — | — | 0.002 | — |
| Homoeriodictyol, sodium salt | — | — | — | 0.002 |
| Vanilla flavor | 0.1 | 0.1 | 0.1 | 0.1 |
| UHT milk, 1.5% fat | | to 100 | | |

The ingredients were mixed, milk was added, stirred well, filled in bottles and stored cold at 5° C.

Practical Example 18

Reduced-Sugar Tomato Ketchup

Comparative preparation with sugar (A)
Comparative preparation with reduced amount of sugar (B)
Preparations according to the invention (C-I)

|  | Preparation (amounts in wt %) | | | | | | | |
| --- | --- | --- | --- | --- | --- | --- | --- | --- |
| Ingredient | A | B | C | E | F | G | H | I |
| Common salt | 2 | 2 | 2 | 2 | 2 | 2 | 2 | 2 |
| Starch, Farinex WM 55 | 1 | 1 | 1 | 1 | 1 | 1 | 1 | 1 |
| Sucrose | 12 | 9.6 | 9.2 | 8.4 | 9.6 | 9.6 | 8.4 | 4.2 |
| Tomato double concentrate | 40 | 40 | 40 | 40 | 30 | 30 | 30 | 30 |
| Glucose syrup 80 Brix | 18 | 18 | 18 | 18 | 18 | 18 | 18 | 18 |
| Brandy vinegar 10% | 7 | 7 | 7 | 7 | 3 | 3 | 3 | 3 |
| Rebaudioside A 98% | — | — | — | — | — | — | — | 0.05 |
| Compound (15) + (16) (ratio 1:1) | — | — | 0.01 | 0.005 | 0.005 | 0.01 | 0.005 | 0.01 |
| Extract of *Rubus suavissimus* (e.g. from PlantExtract) containing 5 wt % rubusoside, relative to the total weight of the extract | — | — | — | — | — | — | 0.01 | — |
| Hesperetin 2.5% in 1,2-propylene glycol | — | — | — | — | 0.1 | — | 0.1 | — |
| Phloretin 2.5% in 1,2-propylene glycol | — | — | — | 0.2 | 0.2 | — | — | 0.3 |
| Water | | | | to 100 | | | | |

The ingredients are mixed in the order stated and the finished ketchup is homogenized with a stirrer, filled in bottles and sterilized.

Practical Example 19

Reduced-Sugar Ice Cream

Comparative preparation with sugar (A)
Comparative preparation with reduced amount of sugar (B)
Preparations according to the invention (C-F)

|  | Preparation (content in wt %) | | | | | |
|---|---|---|---|---|---|---|
| Ingredient | A | B | C | D | E | F |
| Plant fat, melting range 35-40° C. | 20.00 | 20.00 | 20.00 | 20.00 | 20.00 | 20.00 |
| Sugar (sucrose) | 12.00 | 8.00 | 8.00 | 8.00 | 8.00 | 8.00 |
| Skim milk powder | 5.00 | 5.00 | 5.00 | 5.00 | 5.00 | 5.00 |
| Glucose syrup 72% dry matter | 5.00 | 5.00 | 5.00 | 5.00 | 5.00 | 5.00 |
| Emulsifier SE 30 (Grindstedt Products, Denmark) | 0.65 | 0.65 | 0.65 | 0.65 | 0.65 | 0.65 |
| Flavoring, containing 0.1% diacetyl and 1% vanillin | 0.20 | 0.20 | 0.20 | 0.20 | 0.20 | 0.20 |
| Compound (23) + (24) (ratio 1:1) | — | — | 0.01 | 0.0075 | 0.01 | 0.003 |
| Extract of *Rubus suavissimus* (e.g. from Plant-Extract) containing 5 wt % rubusoside, relative to the total weight of the extract | — | — | — | — | — | 0.010 |
| Hesperetin 2.5% in 1,2-propylene glycol | — | — | — | 0.10 | — | 0.10 |
| Phloretin 2.5% in 1,2-propylene glycol | — | — | — | — | 0.05 | 0.05 |
| Skim milk | | | | to 100 | | |

The plant fat was heated to 58° C. Skim milk and glucose syrup were heated to 55° C. and sugar, skim milk powder and emulsifier and flavoring were added and the mixture was added to the plant fat. The mixture was homogenized using a flow-through high-pressure homogenizer (180/50 bar). The resultant mass was heat-treated for 1 min at 78° C., then cooled to 2-4° C. and incubated at this temperature for 10 h for maturation. Then the matured mass was filled and stored frozen at −18° C.

Practical Example 20

Ice Cream Suitable for Diabetics

An ice cream suitable for diabetics was made from the following ingredients and filled in 95-mL portions in beakers:
thickened skim milk, fructose syrup, strawberry pieces and strawberry puree (15 wt %), plant fat, diet chocolate chips (3.5 wt %, with soybean lecithin emulsifier), whey product, beetroot juice, carob flour, guar flour, carrageenan, emulsifier (E 471), gelatin, citric acid acidifying agent, 0.1 wt % strawberry flavor (containing a total of 5 wt % of compounds (23)+(24) (ratio 1:1), relative to the total weight of the strawberry flavor), carotene dye.
Nutritive value (per 95 mL):
protein 1.8 g, carbohydrates 13.3 g (including fructose 9.5 g), fat 4.2 g.

Practical Example 21

Diet Chocolate Based on Maltitol

Chocolate suitable for diabetics was made from the following ingredients and molded in rectangular slabs:
maltitol, hazelnut paste, cocoa butter, skim milk powder, cocoa mass, inulin, purified butterfat, soybean lecithin emulsifier, 0.1 wt % vanilla flavor (containing vanilla pod extract, vanillin and a total of 3 wt % of compounds (15)+(16) (ratio 1:1) and a total of 3 wt % of compounds (17)+(18) (ratio 1:1), relative to the total weight of the vanilla flavor).
Nutritive value (per 100 g):
protein 8 g, carbohydrates 43 g (including maltitol 34 g), fat 34 g.

Practical Example 22

Diet Chocolate Based on Fructose

Chocolate suitable for diabetics was made from the following ingredients and molded in rectangular slabs:
cocoa mass, fructose, skim milk powder, cocoa butter, inulin, purified butterfat, soybean lecithin emulsifier, walnuts, table salt, 0.1 wt % vanilla flavor (containing vanillin and a total of 3 wt % of compound (23)+(24) (ratio 1:1), relative to the total weight of the vanilla flavor).
Nutritive value (per 100 g):
protein 8.8 g, carbohydrates 34 g (including fructose 23 g, lactose 7.5 g, sucrose 1.4 g), fat 36 g; ballast substances 18.5 (including 12.2 g inulin); sodium: 0.10 g. Proportion of cocoa at least 50 wt %.

Practical Example 23

Reduced-Sugar Muesli Mixture

Comparative preparation with sugar (A)
Preparation according to the invention with reduced proportion of sugar (B)

| No. |  | A (wt %) | B (wt %) |
|---|---|---|---|
| 1 | Rolled oats | 17.00 | 19.00 |
| 2 | Crunchy Rolled Oats Cluster | 10.00 | 12.00 |
| 3 | Rice Crispies | 16.90 | 17.80 |
| 4 | Cornflakes | 16.50 | 17.50 |
| 5 | Currants | 3.50 | 3.50 |
| 6 | Hazelnuts, chopped | 2.50 | 2.50 |
| 7 | Glucose syrup from wheat, DE 30 | 9.50 | 9.50 |
| 8 | Sucrose | 20.00 | 14.00 |
| 9 | Water | 4.00 | 4.03 |

65
-continued

| No. | | A (wt %) | B (wt %) |
|---|---|---|---|
| 10 | Citric acid powder, anhydrous | 0.10 | 0.10 |
| 11 | Aromatic composition D from practical example 2 | — | 0.07 |

Mix each of the ingredients No. 1 through 6 in a rotating-drum mixer (Mix 1). Heat each of the ingredients No. 7 through 9 and add ingredient No. 10 (and in Recipe B, also add ingredient No. 11) (Mix 2). In each case add Mix 2 to Mix 1 and mix well. Finally put the resultant muesli mixture on a baking tray and dry in an oven at 130° C. for 8 minutes.

Practical Example 24

Reduced-Sugar Fruit Gums

Comparative preparation with sugar (A)
Preparation according to the invention with reduced proportion of sugar (B)

| | A (wt %) | B (wt %) |
|---|---|---|
| Water | 23.70 | 25.70 |
| Sucrose | 34.50 | 8.20 |
| Glucose syrup, DE 40 | 31.89 | 29.89 |
| Iso Syrup C* Tru Sweet 01750 (Cerestar GmbH) | 1.50 | 2.10 |
| Gelatin 240 Bloom | 8.20 | 9.40 |
| Polydextrose (Litesse ® Ultra, Danisco Cultor GmbH) | — | 24.40 |
| Yellow and red dye | 0.01 | 0.01 |
| Citric acid | 0.20 | 0.2 |
| Cherry flavor, containing a total of 4 wt % of compounds (23) + (24) (ratio 1:1), and 0.3 wt % phloretin, relative to the cherry flavor | — | 0.10 |

Polydextrose is a polysaccharide with low calorific value, which itself is not sweet-tasting.

Practical Example 25

Chocolate-Cappuccino Ice Cream

Comparative preparation with sugar (A)
Preparation according to the invention with reduced proportion of sugar (B)

| | A (wt %) | B (wt %) |
|---|---|---|
| Glucose-fructose-syrup | 14.30 | 14.30 |
| Sucrose | 10.00 | 7.50 |
| Skim milk powder | 5.00 | 5.00 |
| Cream (36% fat) | 24.00 | 24.00 |
| Emulsifier and stabilizer Cremodan ® 709VEG (Danisco) | 0.50 | 0.50 |
| Cocoa powder | 5.975 | 5.975 |
| Carrageenan | 0.025 | 0.025 |
| Water | 40.20 | 42.50 |
| Cappuccino flavor, containing a total of 2 wt % of compounds (15) + (16) (ratio 1:1) and 1 wt % homoeriodictyol, sodium salt, relative to the total flavoring material | — | 0.20 |

The invention claimed is:

1. A method of imparting or enhancing sweetness in an orally consumable composition comprising adding to the orally consumable composition:

(a) a compound of Formula (I), or a physiologically acceptable salt thereof, in an amount sufficient to impart or enhance sweetness in the orally consumable composition:

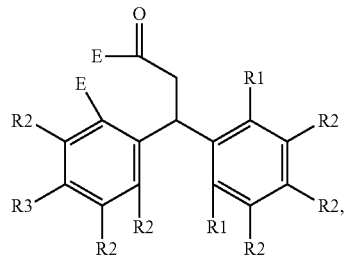

(I)

wherein
E denotes in each case OH or both E together denote O,
R1, independently of one another, denotes hydrogen or ORa, wherein Ra is hydrogen, C1-C5 alkyl or C2-C5 alkenyl,
R2, independently of one another, denotes hydrogen or ORb, wherein Rb is hydrogen, C1-C5 alkyl or C2-C5 alkenyl, wherein optionally two directly adjacent residues R1 and/or R2 together represent a group OCH2O, and
R3 denotes a residue ORx, wherein Rx is C1-C5 alkyl or C2-C5 alkenyl;
thereby imparting or enhancing the sweetness of the orally consumable composition.

2. The method according to claim 1, wherein:
R1, independently of one another, denotes hydrogen or hydroxyl,
R2, independently of one another, denotes hydrogen, hydroxyl, methoxy, ethoxy, n-propoxy, iso-propoxy, n-butoxy, iso-butoxy, tert-butoxy or ORb, wherein Rb is C5-alkenyl, wherein optionally two directly adjacent residues R2 together represent a group OCH2O,
R3 denotes methoxy, ethoxy, n-propoxy, iso-propoxy, n-butoxy, iso-butoxy, tert-butoxy or ORc, wherein Rc is C5-alkenyl.

3. The method according to claim 1, wherein the compound of formula (I) is a compound of formula (II), a physiologically acceptable salt thereof:

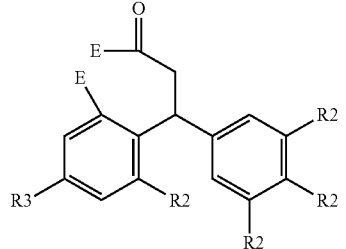

(II)

wherein
E denotes in each case OH or both E together denote O,
R2, independently of one another, denotes hydrogen, hydroxyl, methoxy, ethoxy, n-propoxy or iso-propoxy, wherein optionally two directly adjacent residues R2 together represent a group OCH2O, and R3 denotes methoxy, ethoxy, n-propoxy, iso-propoxy, n-butoxy, iso-butoxy, tert-butoxy or ORc, wherein Rc is C5-alkenyl.
4. The method according to claim 1, wherein the compound of Formula (I) is selected from the group consisting of:
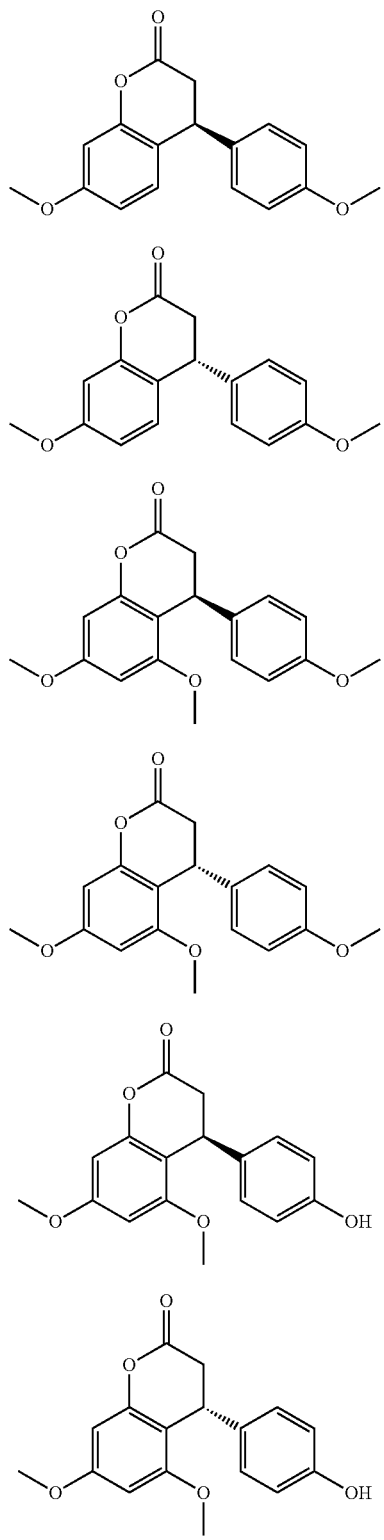
(1)
(2)
(3)
(4)
(5)
(6)
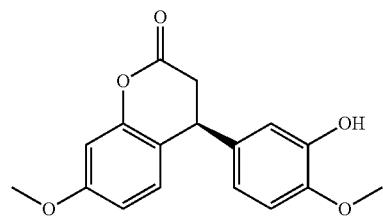
(7)
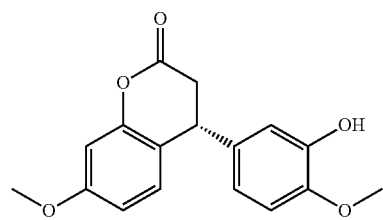
(8)
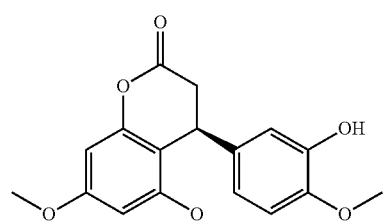
(9)
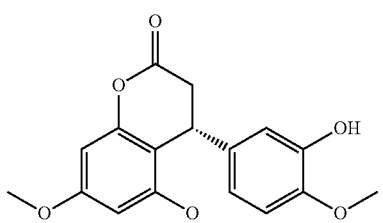
(10)
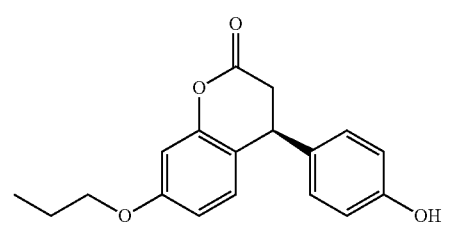
(11)
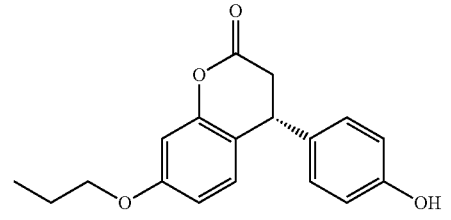
(12)
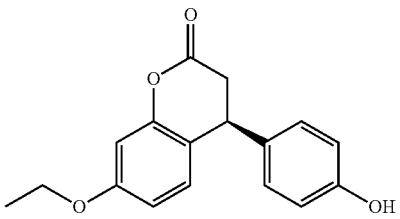
(13)

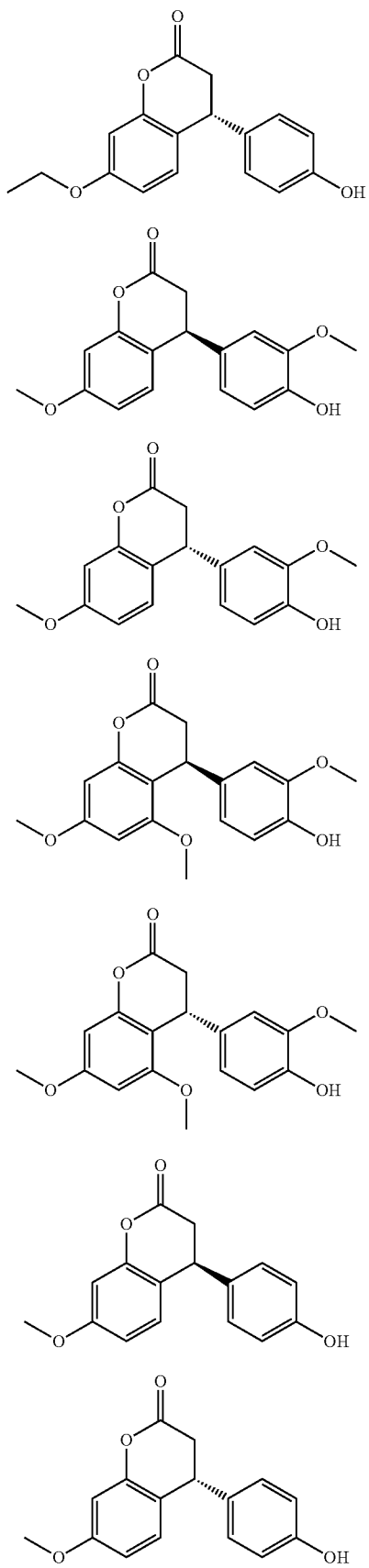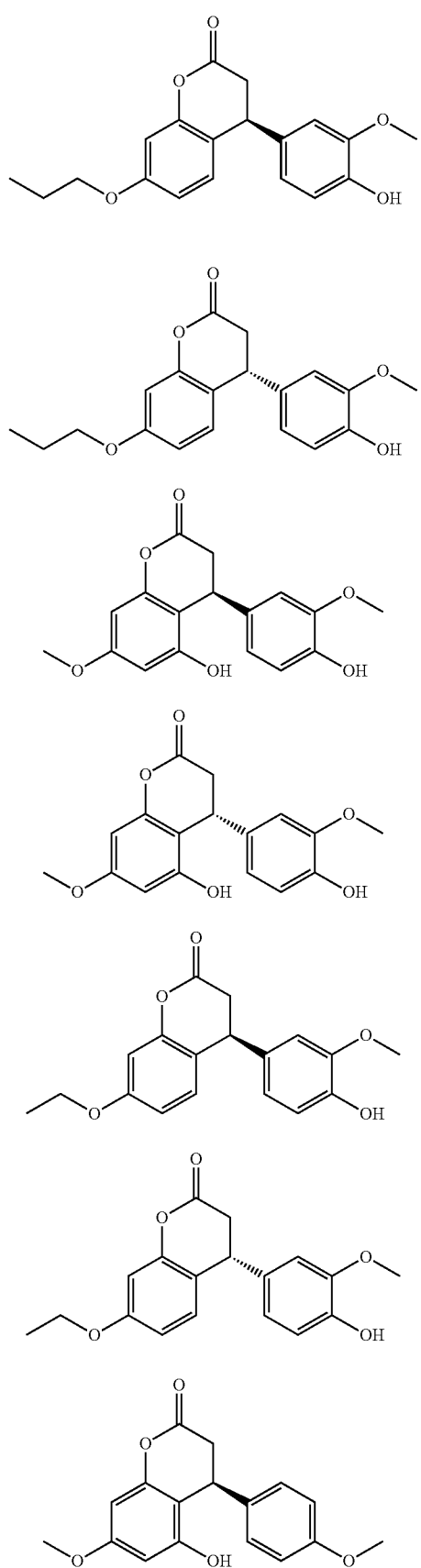

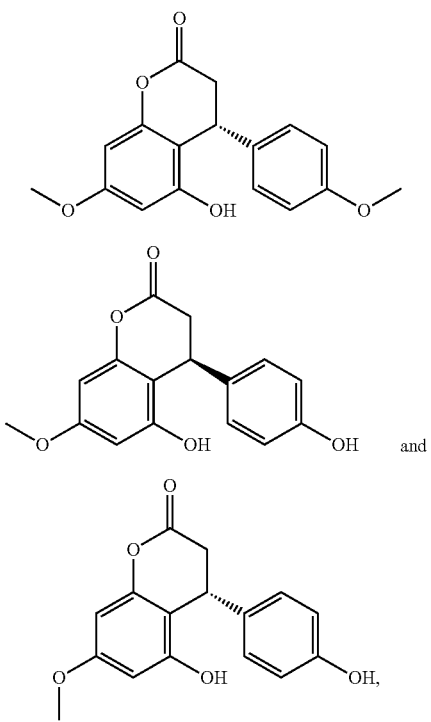

or a physiologically acceptable salts thereof.

5. The method according to claim 1, wherein an oppositely charged cation of the physiologically acceptable salt is present in the composition and selected from the group consisting of Na+, K+, NH4+, Ca2+, Mg2+, Al3+ and Zn2+.

6. The method according to claim 1, wherein the orally consumable composition comprises:
(b) a sweet tasting or smelling substance, which is not a compound of formula (I) or a physiologically acceptable salt thereof; and/or
(c) a substance that is both sweet and bitter tasting, which is not a compound of formula (I) or a physiologically acceptable salt thereof.

7. The method according to claim 6, wherein the orally consumable composition comprises (b), a sweet tasting or smelling substance, which is not a compound of formula (I), or a physiologically acceptable salt thereof, selected from the group consisting of:
(b1) a sweet aromatic substance,
(b2) a carbohydrate,
(b3) a sugar alcohol,
(b4) a naturally occurring sweetener, and
(b5) a synthetic sweet-tasting substance.

8. The method according to claim 7, wherein the orally consumable composition comprises (b1), a sweet aromatic substance, selected from the group consisting of vanillin, ethylvanillin, 2-hydroxy-4-methoxybenzaldehyde, ethylvanillinisobutyrate (=3-ethoxy-4-isobutyryloxybenzaldehyde), 2,5-dimethyl-4-hydroxy-3(2H)-furanone, homofuraneol, 2-ethyl-5-methyl-4-hydroxy-5-methyl-3(2H)-furanone, homofuronol (2-ethyl-5-methyl-4-hydroxy-3(2H)-furanone and 5-ethyl-2-methyl-4-hydroxy-3(2H)-furanone), maltol, ethylmaltol, coumarin, a gamma-lactone, a delta-lactone, methyl sorbate, divanillin, 4-hydroxy-2(or 5)-ethyl-5(or 2)-methyl -3(2H)furanone, 2-hydroxy-3-methyl-2-cyclopentenone, 3-hydroxy-4,5-dimethyl-2(5H) -furanone, a fruit ester, a fruit lactone, 4-(p-hydroxyphenyl)-2-butanone, 1,1-dimethoxy -2,2,5-trimethyl-4-hexane, 2,6-dimethyl-5-hepten-1-al, and phenyl acetaldehyde.

9. The method according to claim 8, wherein the orally consumable composition comprises (c), a substance that is both sweet and bitter tasting, which is not a compound of formula (I) or a physiologically acceptable salt thereof, selected from the group consisting of a steviol glycoside, rubusoside, a dulcoside, a mogroside, phyllodulcin, glycyrrhetin acid, extracts of Stevia ssp., Luo Han Guo, Rubus suavissimus, Hydrangea dulcis, Glycyrrhyza glabra, magap, sodium cyclamate, acesulfame-K, neohesperidin dihydrochalcone, naringin dihydrochalcone, saccharin, saccharin sodium salt, aspartame, superaspartame, neotame, alitame, sucralose, lugduname, carrelame, sucrononate and sucrooctate.

10. The method according to claim 7, wherein the orally consumable composition comprises (b2), a carbohydrate, selected from the group consisting of sucrose, trehalose, lactose, maltose, melezitose, melibiose, raffinose, Palatinose, lactulose, D-fructose, D-glucose, D-galactose, L-rhamnose, D-sorbose, D-mannose, D-tagatose, D-arabinose, L-arabinose, D-ribose, D-glyceraldehydes, and a maltodextrin.

11. The method according to claim 10, wherein the carbohydrate is sucrose.

12. The method according to claim 7, wherein the orally consumable composition comprises (b3), a sugar alcohol, selected from the group consisting of glycerol, erythritol, threitol, arabitol, ribitol, xylitol, sorbitol, mannitol, maltitol, isomaltitol, dulcitol, and lactitol.

13. The method according to claim 7, wherein the orally consumable composition comprises (b4), a naturally occurring sweetener, selected from the group consisting of miraculin, monellin, mabinlin, thaumatin, curculin, brazzein, pentadin, D-phenylalanine, D-tryptophan, neohesperidin dihydrochalcone, naringin dihydrochalcone, stevioside, steviolbioside, rebaudiosides, rebaudioside B, rebaudioside C, rebaudioside D, rebaudioside E, rebaudioside F, rebaudioside G, rebaudioside H, dulcosides, rubusoside, suavioside A, suavioside B, suavioside G, suavioside H, suavioside I, suavioside J, baiyunoside 1 baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartin, telosmoside $A_{15}$, periandrin I-V, pterocaryosides, cyclocaryosides, mukuroziosides, trans-anethole, trans-cinnamaldehydes, bryonosides, bryonosides, bryonodulcosides, carnosiflosidenes, scandenosides, gypenosides, trilobatin, phloridzin, dihydroflavanols, hematoxylin, cyanin, chlorogenic acid, albiziasaponin, telosmosides, gaudichaudioside, mogrosides, mogroside V, hernandulcines, monatin, phyllodulcin, glycyrrhetin acid, and the physiologically acceptable salts of these compounds, extracts of Thaumatococcus (katemphe), Stevia ssp., swingle (Momordica or Siratia grosvenorii, Luo-Han-Guo), Glycerrhyzia ssp., Rubus ssp., Lippia dulcis; and Mycetia balansae.

14. The method according to claim 7, wherein the orally consumable composition comprises (b5), a synthetic sweet-tasting substance, selected from the group consisting of magap, sodium cyclamate or other physiologically acceptable salts of cyclamic acid, acesulfame-K or other physiologically acceptable salts, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

* * * * *